(12) United States Patent
Gerdes et al.

(10) Patent No.: US 10,106,845 B2
(45) Date of Patent: *Oct. 23, 2018

(54) METHODS FOR MULTIPLEXING AMPLIFICATION REACTIONS

(71) Applicant: APPLIED BIOSYSTEMS, LLC, Carlsbad, CA (US)

(72) Inventors: John Gerdes, Littleton, CO (US); Elaine Best, Lafayette, CO (US); Jeffrey M. Marmaro, Sarasota, FL (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/293,387

(22) Filed: Oct. 14, 2016

(65) Prior Publication Data

US 2017/0130259 A1 May 11, 2017

Related U.S. Application Data

(60) Division of application No. 14/302,980, filed on Jun. 12, 2014, now Pat. No. 9,481,907, which is a continuation of application No. 13/619,436, filed on Sep. 14, 2012, now Pat. No. 8,815,546, which is a continuation of application No. 11/944,169, filed on Nov. 21, 2007, now Pat. No. 8,304,214, which is a division of application No. 11/176,795, filed on Jul. 7, 2005, now Pat. No. 7,531,328, which is a division of application No. 10/441,158, filed on May 19, 2003, now Pat. No. 7,087,414, which is a continuation-in-part of application No. 09/589,560, filed on Jun. 6, 2000, now Pat. No. 6,605,451.

(51) Int. Cl.
| | |
|---|---|
| *C12P 19/34* | (2006.01) |
| *C12Q 1/686* | (2018.01) |
| *C12Q 1/6827* | (2018.01) |
| *C12Q 1/6844* | (2018.01) |
| *C12Q 1/689* | (2018.01) |
| *C12Q 1/6806* | (2018.01) |

(52) U.S. Cl.
CPC ........... *C12Q 1/686* (2013.01); *C12Q 1/6806* (2013.01); *C12Q 1/689* (2013.01); *C12Q 1/6827* (2013.01); *C12Q 1/6844* (2013.01); *C12Q 2600/156* (2013.01); *C12Q 2600/16* (2013.01)

(58) Field of Classification Search
CPC ................. C12Q 1/6844; C12Q 1/689; C12Q 2537/143; C12Q 2549/113; C12Q 1/686; C12Q 2600/16; C12Q 1/6806; C12Q 1/6827; C12Q 2531/101; C12Q 2531/113; C08K 5/18; C08L 77/00
USPC ...................................................... 435/91.2
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,965,188 A | 10/1990 | Mullis et al. |
| 5,035,996 A | 7/1991 | Hartley |
| 5,130,238 A | 7/1992 | Malek et al. |
| 5,298,392 A | 3/1994 | Atlas et al. |
| 5,354,668 A | 10/1994 | Auerbach |
| 5,422,252 A | 6/1995 | Walker et al. |
| 5,427,930 A | 6/1995 | Birkenmeyer et al. |
| 5,437,976 A | 8/1995 | Utermohlen |
| 5,455,166 A | 10/1995 | Walker |
| 5,512,430 A | 4/1996 | Gong |
| 5,538,848 A | 7/1996 | Livak et al. |
| 5,582,989 A | 12/1996 | Caskey et al. |
| 5,593,838 A | 1/1997 | Zanzucchi et al. |
| 5,612,473 A | 3/1997 | Wu et al. |
| 5,624,825 A | 4/1997 | Walker et al. |
| 5,705,365 A | 1/1998 | Ryder et al. |
| 5,716,784 A | 2/1998 | Di Cesare |
| 5,723,591 A | 3/1998 | Livak et al. |
| 5,728,526 A | 3/1998 | George, Jr. et al. |
| 5,736,365 A | 4/1998 | Walker et al. |
| 5,738,995 A | 4/1998 | Wu et al. |
| 5,750,338 A | 5/1998 | Collin et al. |
| 5,776,682 A | 7/1998 | First et al. |

(Continued)

FOREIGN PATENT DOCUMENTS

| | | |
|---|---|---|
| AU | 2001265327 | 1/2006 |
| EP | 0320308 | 6/1989 |

(Continued)

OTHER PUBLICATIONS

Assays-by-Design Service [Online], "[retrieved on May 13, 2003], Retrieved from the Applied Biosystems using the Internet", <URL: http://www.applied biosystems.com/products/productdetail.cfm?prod_id=761.<., May 13, 2005.

Assays-on-Demand, "Gene Expression Products [online], [retrieved on May 13, 2003], Retrieved from the Applied Biosystems using Internet", <http://www.appliedbiosystems.com/products/productdetail.cfm?prod_id=1101>., May 13, 2003.

Assays-on-Demand, "SNP Genotyping Products [online], [retrieved on May 13, 2003], Retrieved from the Applied Biosystems using Internet", <http://www.appliedbiosystems.com/products/productdetail.cfm?prod_id=1141>, May 13, 2003.

(Continued)

*Primary Examiner* — Cynthia B Wilder

(57) ABSTRACT

A two-step multiplex amplification reaction includes a first step which truncates the standard initial multiplex amplification round to "boost" the sample copy number by only a 100-1000 fold increase in the target. Following the first step the product is divided into optimized secondary single amplification reactions, each containing one of the primer sets that were used previously in the first or multiplexed booster step. The booster step can occur using an aqueous target nucleic acid or using a solid phase archived nucleic acid. In particular, nucleic acid sequences that uniquely identify *E. Coli* were identified using the multiplex amplification method.

20 Claims, 4 Drawing Sheets

Specification includes a Sequence Listing.

(56) References Cited

U.S. PATENT DOCUMENTS

| | | | |
|---|---|---|---|
| 5,843,660 | A | 12/1998 | Schumm et al. |
| 5,858,673 | A | 1/1999 | Price et al. |
| 5,882,856 | A | 3/1999 | Shuber et al. |
| 5,888,736 | A | 3/1999 | Lacroix et al. |
| 5,912,148 | A | 6/1999 | Eggerding |
| 5,952,173 | A | 9/1999 | Hansmann et al. |
| 5,955,268 | A | 9/1999 | Granados |
| 5,981,180 | A | 11/1999 | Chandler et al. |
| 5,989,809 | A | 11/1999 | Stavrianopoulos |
| 6,001,571 | A | 12/1999 | Mandecki |
| 6,013,440 | A | 1/2000 | Lipshutz et al. |
| 6,027,889 | A | 2/2000 | Barany et al. |
| 6,090,558 | A | 7/2000 | Butler et al. |
| 6,153,425 | A | 11/2000 | Kozwich et al. |
| 6,207,372 | B1 | 3/2001 | Shuber |
| 6,270,967 | B1 | 8/2001 | Whitcombe et al. |
| 6,403,303 | B1 | 6/2002 | Shipman et al. |
| 6,440,661 | B1 | 8/2002 | Ogreid et al. |
| 6,472,156 | B1 | 10/2002 | Wittwer et al. |
| 6,605,451 | B1 | 8/2003 | Marmaro et al. |
| 6,618,679 | B2 | 9/2003 | Loebriein et al. |
| 7,087,414 | B2 | 8/2006 | Gerdes et al. |
| 7,118,910 | B2 | 10/2006 | Unger et al. |
| 7,531,328 | B2 | 5/2009 | Gerdes et al. |
| 8,304,214 | B2 | 11/2012 | Gerdes et al. |
| 8,323,897 | B2 | 12/2012 | Andersen et al. |
| 8,815,546 | B2 | 8/2014 | Gerdes et al. |
| 9,206,475 | B2 | 12/2015 | Gerdes et al. |
| 2002/0182622 | A1 | 12/2002 | Nakamura et al. |
| 2003/0186246 | A1 | 10/2003 | Willey et al. |
| 2004/0146897 | A1 | 7/2004 | Parker et al. |
| 2005/0019893 | A1 | 1/2005 | Huletsky et al. |
| 2005/0048531 | A1 | 3/2005 | Mittman et al. |
| 2005/0175987 | A1 | 8/2005 | Jansen et al. |
| 2015/0125869 | A1 | 5/2015 | Gerdes et al. |

FOREIGN PATENT DOCUMENTS

| | | |
|---|---|---|
| EP | 0364255 | 4/1990 |
| EP | 0624643 | 11/1994 |
| EP | 1026258 | 8/2000 |
| EP | 2194147 | 7/2015 |
| KR | 20020000280 | 6/2000 |
| WO | WO-1998/024928 | 6/1998 |
| WO | WO-1998/046797 | 10/1998 |
| WO | WO-1999/064624 | 12/1999 |
| WO | WO-2000/044935 | 8/2000 |
| WO | WO-2001/032909 | 5/2001 |
| WO | WO-01/55454 | 8/2001 |
| WO | WO-2001/061033 | 8/2001 |
| WO | WO-2001/61034 | 8/2001 |
| WO | WO-2001/94634 | 12/2001 |
| WO | WO-2002/090505 | 11/2002 |
| WO | WO-2004/051218 | 6/2004 |

OTHER PUBLICATIONS

Bej, A K. et al., "Detection of Coliform Bacteria in Water by Polymerase Chain Reaction and Gene Probes", *Applied and Environmental Microbiology*, vol. 56, No. 2,, Feb. 1990, 307-314.

Bej, A. K. et al., "Detection of Coliform Bacteria and *Escherichia coli* by Multiplex Polymerase Chain Reaction: Comparison With Defined Substrate and Plating Methods for Water Quality Monitoring", *Applied and Environmental Microbiology*, vol. 57, No. 8,, Aug. 1991, 2429-2432.

Bej, A. K. et al., "Detection of *Escherichia coli* and *Shigella* spp. in Water by Using the Polymerase Chain Reaction and Gene Probes for uid", *Applied and Environmental Microbiology*, vol. 57, No. 4,, Apr. 1991, 1013-1017.

Bej, A. K. et al., "Multiplex PCR Amplification and Immobilized Capture Probes for Detection of Bacterial Pathogens and Indicators in Water", *Molecular and Cellular Probes*, vol. 4, Issue 5, Academic Press, London, GB,, Oct. 1990, 353-365.

Borg, K. L. et al., "Detection of cytomegalovirus using 'boosted' nested PCR.", *Molecular and Cellular Probes*, vol. 9, No. 4, England,, Aug. 1995, 251-257.

Chamberlain, Jeffrey et al., "Deletion screening of the Duchenne muscular dystrophy locus via multiplex DNA amplification", *Nucl. Acids Res.*, vol. 16, No. 23, 1988, 11141-11155.

D'Aquila, Richard T. et al., "Maximizing sensitivity and specificity of PCR by pre-amplification heating", *Nucleic Acids Research*, vol. 19, No. 13, Oxford University Press,, Jul. 11, 1991, 3749.

Dolganov, G., "A Novel Method of Gene Transcript Profiling in Airway Biopsy Homogenates Reveals Increased Expression of a Na+—K+—Cl- Cotransporter (NKCC1) in Asthmatic Subjects", *Genome Research*, 11, 2001, 1473-1483.

Edwards, M. C. et al., "Multiplex PCR: Advantages, Development, and Applications", *PCR Methods and Applications*, vol. 3, No. 4, Cold Spring Harbor Laboratory Press, US,, Feb. 1994, S65-S75.

EP 03796461, "Partial European Search Report", dated Apr. 6, 2006.

EP 03796461, "Supplementary European Search Report", dated Jun. 30, 2006.

EP08020322, "EP search report", dated Jan. 29, 2009, 7 pages.

EP09016059, "Search Report", dated Apr. 29, 2010, 5 pages.

EP10182843.2, "Extended European Search Report", dated Jun. 20, 2011, 14 pages.

EP14164752.9, "Extended European Search Report dated Oct. 12, 2015", Oct. 12, 2015, 12 Pages.

EP15177617.6, "Extended European Search Report dated Feb. 26, 2016", Feb. 26, 2016, 6 pages.

Exner, M. et al., "Sensitivity of multiplex real-time PCR reactions, using the LightCycler and the ABI Prism 7700 Sequence Detection System, is dependent on the concentration of the DNA polymerase", *Mol. Cell Probes*, 16:, Oct. 2002, 351-357.

Gonin, P. et al., "Performance of a multiplex PCR for the determination of Haemophilus influenzae capsular types in the clinical microbiology laboratory", *Diagnostic Microbiology and Infectious Disease*, vol. 37, No. 1, US,, May 2000, 1-4.

Grace, M. et al., "Degradable dUMP Outer Primers in Merged Tandem (M/T)-Nested PCR: Low- and Single-Copy DNA Target Amplification", vol. 263, Article No. AB982771, 1998, 85-92.

Graves, L. M. et al., "Universal Bacterial DNA Isolation Procedure", *Diagnostic Molecular Microbiology; Principles and Applications*, American Society for Microbiology, Washington, D.C.,, 1993, 617-621.

Green, D et al., "Detection of faecal pollution in water by an *Escherichia coli* uidA gene probe", *Journal of Microbiological Methods*, vol. 13, Issue 3,, Jul. 1991, 207-214.

Heid, et al., "Real Time Quantitative PCR", *Genome Research, Cold Spring Harbor Laboratory Press*, Woodbury, NY, vol. 6 (10), Oct. 1996, 986-994.

Henegariu, et al., "Multiplex PCR: Critical Parameters and Step-by-Step Protocol", *BioTechniques*, vol. 23, No. 3, 1997, 504-511.

Henegariu, et al., "Multiplex PCR: Critical Parameters and Step-By-Step Protocol", *Biotechniques*, vol. 23, No. 3, Sep. 1997, 504-511.

Jayaraman, et al., "A PCR-mediated Gene Synthesis strategy involving assamply of oligonucleotides resenting only one of the strands", *BioTechniques*, vol. 12, No. 3, 1992, 392-398.

Kainz, Peter, "The PCR plateau phase—towards an understanding of its limitations", *Biochimica et Biophysica Acta*, vol. 1494, 2000, 23-27.

Kaltenboeck, "Two-Step Polymerase Chain Reactions and Restriction Endonuclease Analyses Detect and Differentiate ompA DNA of *Chlamydia* spp", *Journal of Clinical Microbiology*, vol. 30, No. 5, American Society for Microbiology,, May 1992, 1098-1104.

Kato, K., "Laboratory Manual PCR- Study and Application to Clinical Diagnosis", *First Edition Takara Shuzo Co. Ltd*, 1996, 73-81.

Li, D. et al., "Multiplex co-amplification of 24 retinoblastoma gene exons after pre-amplification by long-distance PCR", *Nucleic Acids Research*, 24(3), 1996, 538-539.

(56) References Cited

OTHER PUBLICATIONS

Lin, Z et al., "Multiplex Genotype Determination at a Large Number of Gene Loci", *Proceedings of the National Academy of Sciences of the United States*, vol. 93, No. 6, Genetics, USA,, Mar. 1996, 2582-2587.

Liu, Q, "Subcycling-PCR for Multiplex Long-Distance Amplification of Regions with High and Low GC Content: Application to the Inversion Hotspot in the Factor VIII Gene", *BioTechniques*, vol. 25, No. 6, Dec. 1998, 1022-1028.

Longo, M et al., "Use of uracil DNA glycosylase to control carry-over contamination in polymerase chain reactions", *Gene*, vol. 93,, 1990, 125-128.

Lupo, M et al., "Gene Controlling L-Glutamic Acid Decarboxylase Synthesis in *Escherichia coli* K-12", *Journal of Bacteriology*, vol. 103, No. 2, American Society for Microbiology, USA,, Aug. 1970, 382-386.

Martell, M et al., "High-Throughput Real-Time Reverse Transcription-PCR Quantitation of Hepatitis C Virus RNA", *Journal of Clinical Microbiology*, vol. 37, No. 2, American Society for Microbiology, Feb. 1999, 327-332.

Min, J. et al., "Highly Sensitive and Specific Detection of Viable *Escherichia coli* in Drinking Water", *Analytical Biochemistry*, vol. 303, Issue 2, Elsevier Science, USA,, Apr. 15, 2002, 186-193.

Ohnishi, et al., "A high-throughput SNP typing system for genome-wide association studies", *J. Hum. Genet.*, 46:, 2001, 471-477.

Peirson, S. N., "Experimental validation of novel and conventional approaches to quantitative real-time PCR data analysis", *Nucleic Acids Res.*, 31(14), 2003, e73.

Picard, C. et al., "Detection and Enumeration of Bacteria in Soil by Direct DNA Extraction and Polymerase Chain Reaction", *Applied and Environmental Microbiology*, vol. 58, No. 9,, Sep. 1992, 2717-2722.

Rice, et al., "Detection of *Escherichia coli* in Water Using a Colorimetric Gene Probe Assay", *Journal of Environmental Science and Health*, vol. 30, Issue 5,, 1995, 1059-1067.

Roche Diagnostics GmbH, "RealTime ready cDNA Pre-Amp Master", *Roche Applied Science Catalog* No. 06 720 455 001, Version 01, Sep. 2012, 16 pages.

Ruano, G et al., "Coupled amplification and sequencing of genomic DNA", *Proceedings of the National Academy of Sciences of the United States of America*, vol. 88,, 1991, 2815-2519.

Ruano, G. et al., "Biphasic Amplification of Very Dilute DNA Samples via 'Booster' PCR", *Nucleic Acids Research*, vol. 17, No. 13, Oxford University Press, Surrey, GB,, Jul. 11, 1989, 5407.

Ruano, G. et al., "Booster PCR: A Biphasic Paradigm for Amplification of a Few Molecules of Target", *Amplifications: A Forum for PCR Users*, Perkin-Elmer Co., Norwalk, CT, US,, Sep. 1989, 12-13.

Rudi, K et al., "A Novel MUltiplex Quantitative DNA Array Based PCR (MQDAPCR)", *Nucleic Acids Research*, 2003, vol. 31, No. 11 e62, Jan. 31, 2008, 1-8.

Saiki, R. K., "The Design and Optimization of the PCR", *PCR Technology, Principles and Applications for DNA Amplification*, Stockton Press, New York, US,, Jan. 1989, 7-16.

Saulnier, P. et al., "Detection of Genes in Feces by Booster Polymerase Chain Reaction", *Journal of Clinical Microbiology*, vol. 30, No. 8, American Society for Microbiology, Aug. 1992, 2080-2083.

Sheridan, G. E. et al., "Detection of mRNA by Reverse Transcription-PCR as an Indicator of Viability in *Escherichia coli* Cells", *Applied and Environmental Microbiology*, vol. 64, No. 4, American Society for Microbiology,, Apr. 1998, 1313-1318.

Shuber, A. et al., "A Simplified Procedure for Developing Multiplex PCRs", *Genome Research*, 5, 1995, 488-493.

Song, Y. et al., "Rapid identification of 11 human intestinal *Lactobacillus* species by multiplex PCR assays using group- and species-specific primers derived from the 16S-23S rRNA intergenic spacer region and its flanking 23S rRNA", *FEMS Microbiology Letters*, vol. 187, No. 2, Federation of European Microbiological Societies, Elsevier Science B.V., Netherlands,, 2000, 167-173.

Tettelin, et al., "Optimized Multiplex PCR: Efficiently Closing a Whole-Genome Shotgun Sequencing Project", *Genomics*, vol. 62, 1999, 500-507.

Tichopad, A et al., "Standardized determination of real-time PCR efficiency from a single reaction set-up", *Nucleic Acids Res.*, 31, 2003, e122.

User Bulletin #2, "ABI Prism 7700 Sequence Detection System. Subject: Relative Quantitation of Gene Expression, Datasheet", *Applied Biosystems*, (updated Oct. 2001), 1997.

Wang, et al., "Large-Scale Identification, Mapping, and Genotyping of Single-Nucleotide Polymorphisms in the Human Genome", *Science*, 280:, 1998, 1077-1082.

Waters, L. C. et al., "Microchip Device for Cell Lysis, Multiplex PCR Amplification, and Electrophoretic Sizing", *Analytical Chemistry*, vol. 70, No. 1, American Chemical Society, Columbus, US,, 1998, 158-162.

Wistuba, Ignacio I. et al., "Comparison of Molecular Changes in Lung Cancers in HIV-Positive and HIV-Indeterminate Subjects", *JAMA*, vol 279, No. 19, May 20, 1998, pp. 1554-1559.

Wittwer, C. et al., "Real-Time Multiplex PCR Assays", *Methods*, vol. 25,, 2001, 430-442.

Wittwer, C.T. et al., "The LightCycler™: A Microvolume Multisample Fluorimeter with Rapid Temperature Control", *BioTechniques*, vol. 22 (1), Jan. 1997, 176-181.

WO2001/094634, "PCT International Preliminary Examination Report", dated Mar. 4, 2004, 8 pages.

WO2001/094634, "PCT International Search Report", dated Jan. 23, 2003.

WO2004/051218, "PCT International Search Report", dated Dec. 10, 2004.

WO2004/104214, "PCT International Preliminary Report on Patentability", dated Mar. 13, 2006.

WO2004/104214, "PCT International Search Report", dated Jan. 26, 2006.

WO2004/104214, "PCT Written Opinion", dated Mar. 7, 2006.

METHODS FOR MULTIPLEXING AMPLIFICATION REACTIONS

CROSS-REFERENCE TO RELATED APPLICATIONS

The present application is a divisional of U.S. patent application Ser. No. 14/302,980 filed Jun. 12, 2014, now allowed, which is a continuation of U.S. patent application Ser. No. 13/619,436 filed Sep. 14, 2012, now U.S. Pat. No. 8,815,546, which is a continuation of U.S. patent application Ser. No. 11/944,169 filed Nov. 21, 2007, now U.S. Pat. No. 8,304,214, which is a divisional of U.S. patent application Ser. No. 11/176,795 filed Jul. 7, 2005, and entitled "Methods and Devices for Multiplexing Amplification Reactions," (now U.S. Pat. No. 7,531,328) which is a divisional application of U.S. patent application Ser. No. 10/441,158 filed May 19, 2003 and entitled "Methods and Devices for Multiplexing Amplification Reactions" (now U.S. Pat. No. 7,087,414), which is a continuation-in-part of U.S. patent application Ser. No. 09/589,560 filed Jun. 6, 2000, and entitled "Methods and Devices for Multiplexing Amplification Reactions," (now U.S. Pat. No. 6,605,451), all disclosures of which are herein incorporated by reference in their entirety.

BACKGROUND OF THE INVENTION

1. Field of the Invention

The present invention pertains to a two-step multiplex amplification reaction wherein the first step truncates a standard multiplex amplification round to "boost" the sample copy number by only a 100-1000 fold increase in the target. Following the first step of the present invention, the resulting product is divided into optimized secondary single amplification reactions, each containing one of the primer sets that were used previously in the first or multiplexed booster step. In particular, nucleic acid sequences that uniquely identify $E.\ Coli$ were identified using the multiplex amplification method.

2. Description of the State of the Art

Nucleic acid hybridization assays are based on the tendency of two nucleic acid strands to pair at complementary regions. Presently, nucleic acid hybridization assays are primarily used to detect and identify unique DNA and RNA base sequences or specific genes in a complete DNA molecule in mixtures of nucleic acid, or in mixtures of nucleic acid fragments.

Since all biological organisms or specimens contain nucleic acids of specific and defined sequences, a universal strategy for nucleic acid detection has extremely broad applications in a number of diverse research and development areas as well as commercial industries. The identification of unique DNA or RNA sequences or specific genes within the total DNA or RNA extracted from tissue or culture samples may indicate the presence of physiological or pathological conditions. In particular, the identification of unique DNA or RNA sequences or specific genes, within the total DNA or RNA extracted from human or animal tissue, may indicate the presence of genetic diseases or conditions such as sickle cell anemia, tissue compatibility, cancer and precancerous states, or bacterial or viral infections. The identification of unique DNA or RNA sequences or specific genes within the total DNA or RNA extracted from bacterial cultures or tissue containing bacteria may indicate the presence of antibiotic resistance, toxins, viruses, or plasmids, or provide identification between types of bacteria.

The potential for practical uses of nucleic acid detection was greatly enhanced by the description of methods to amplify or copy, with fidelity, precise sequences of nucleic acid found at low concentration to much higher copy numbers, so that they are more readily observed by detection methods.

The original amplification method is the polymerase chain reaction described by Mullis, et al., in U.S. Pat. Nos. 4,683,195; 4,683,202 and 4,965,188, all of which are specifically incorporated herein by reference. Subsequent to the introduction of PCR, a wide array of strategies for amplification has been described. See, for example, U.S. Pat. No. 5,130,238 to Malek, entitled "Nucleic Acid Sequence Based Amplification (NASBA)"; U.S. Pat. No. 5,354,668 to Auerbach, entitled "Isothermal Methodology": U.S. Pat. No. 5,427,930 to Buirkenmeyer, entitled "Ligase Chain Reaction"; and, U.S. Pat. No. 5,455,166 to Walker, entitled "Strand Displacement Amplification (SDA)," all of which are specifically incorporated herein by reference.

In general, diagnosis and screening for specific nucleic acids using nucleic acid amplification techniques has been limited by the necessity of amplifying a single target sequence at a time. In instances where any of multiple possible nucleic acid sequences may be present, performing multiple separate assays by this procedure is cumbersome and time consuming. For example, the same clinical symptoms generally occur due to infection from many etiological agents and therefore requires differential diagnosis among numerous possible target organisms. Cancer prognosis and genetic risk is known to be due to multiple gene alterations. Genetic polymorphism and mutations result from alterations at multiple loci and further demand determination of zygosity. In many circumstances the quantity of the targeted nucleic acid is limited so that dividing the specimen and using separate repeat analyses is often not possible. There is a substantial need for methods enabling the simultaneous analysis of multiple gene targets for the same specimen. In amplification-based methodologies, such methods are referred to as "multiplex reactions."

Chamberlain, et al., (*Nucleic Acid Research*, (1988) 16:11141-11156) first demonstrated multiplex analysis for the human dystrophin gene. Specific primer sets for additional genetic diseases or infectious agents have subsequently been identified. See, Caskey, et al., EP 364,255A3; Caskey, et al., U.S. Pat. No. 5,582,989; and Wu, et al., U.S. Pat. No. 5,612,473 (1997). The strategy for these multiplex reactions was accomplished by careful selection and optimization of specific primers. Developing robust, sensitive and specific multiplex reactions have demanded a number of specific design considerations and empiric optimizations. See, Edwards and Gibbs, *PCR Methods Applic.*, (1994) 3:S65-S75; Henegariu, et al., *Biotechniques*, (1997) 23:504-511. This results in long development times and compromises reaction conditions that reduce assay sensitivity. Because each multiplex assay requires restrictive primer design parameters and empirical determination of unique reaction conditions, development of new diagnostic tests is very costly.

A number of specific problems have been identified that limit multiplex reactions. Incorporating primer sets for more than one target requires careful matching of the reaction efficiencies. If one primer amplifies its target with even slightly better efficiency, amplification becomes biased toward the more efficiently amplified target resulting in inefficient amplification of other target genes in the multiplex reaction. This is called "preferential amplification" and results in variable sensitivity and possible total failure of one or more of the targets in the multiplex reaction. Preferential amplification can sometimes be corrected by carefully matching all primer sequences to similar lengths and GC content and optimizing the primer concentrations, for example by increasing the primer concentration of the less efficient targets. One approach to correct preferential amplification is to incorporate inosine into primers in an attempt to adjust the primer amplification efficiencies (Wu, et al., U.S. Pat. No. 5,738,995 (1998)). Another approach is to design chimeric primers. Each primer contains a 3' region complementary to sequence-specific target recognition and a 5' region made up of a universal sequence. Using the universal sequence primer permits the amplification efficiencies of the different targets to be normalized. See, Shuber, et al., *Genome Research*, (1995) 5:488-493; and U.S. Pat. No. 5,882,856. Chimeric primers have also been utilized to multiplex isothermal strand displacement amplification (Walker, et al., U.S. Pat. Nos. 5,422,252, 5,624,825, and 5,736,365).

Since multiple primer sets are present, multiplexing is frequently complicated by artifacts resulting from cross-reactivity of the primers. In an attempt to avoid this, primer sequences are aligned using computer BLAST or primer design programs. All possible combinations must be analyzed so that as the number of targets increases this becomes extremely complex and severely limits primer selection. Even carefully designed primer combinations often produce spurious products that result in either false negative or false positive results. The reaction kinetics and efficiency is altered when more than one reaction is occurring simultaneously. Each multiplexed reaction for each different specimen type must be optimized for $MgCl_2$ concentration and ratio to the deoxynucleotide concentration, KCl concentration, Taq polymerase concentration, thermal cycling extension and annealing times, and annealing temperatures. There is competition for the reagents in multiplex reactions so that all of the reactions plateau earlier. As a consequence, multiplexed reactions in general are less sensitive than the corresponding simplex reaction.

Another consideration to simultaneous amplification reactions is that there must be a method for the discrimination and detection of each of the targets. Generally, this is accomplished by designing the amplified product size to be different for each target and using gel electrophoresis to discriminate these. Alternatively, probes or the PCR products can be labeled so as to be detectable by spectroscopic, photochemical, biochemical, immunochemical, or chemical means. For example, using multiple fluorescent dyes incorporated with a self-quenching probe design amplification can be monitored in real time. See, Livak, et al., U.S. Pat. Nos. 5,538,848 and 5,723,591; and Di Cesare, U.S. Pat. No. 5,716,784. The number of multiplexed targets is further limited by the number of dye or other label moieties distinguishable within the reaction. As the number of different fluorescent moieties to be detected increases, so does the complexity of the optical system and data analysis programs necessary for result interpretation. Another approach is to hybridize the amplified multiplex products to a solid phase then detect each target. This can utilize a planar hybridization platform with a defined pattern of capture probes (Granados, et al., U.S. Pat. No. 5,955,268), or capture onto a beadset that can be sorted by flow cytometry (Chandler, et al., U.S. Pat. No. 5,981,180).

Due to the summation of all of the technical issues discussed, current technology for multiplex gene detection is costly and severely limited in the number and combinations of genes that can be analyzed. Generally, the reactions multiplex only two or three targets with a maximum of around ten targets. Isothermal amplification reactions are more complex than PCR and even more difficult to multiplex. See, Van Deursen, et al., *Nucleic Acid Research*, (1999) 27:e15.

There is still a need, therefore, for a method which permits multiplexing of large numbers of targets without extensive design and optimization constraints. There is also a further need for a method of detecting a significantly larger number of gene targets from a small quantity of initial target nucleic acid.

Coliform bacteria are introduced into water through either animal or human fecal contamination. Monitoring their levels is mandated to determine the microbiological quality of water. The standards for potable water include less than one total coliform in 100 milliliters potable water (Title 40, Code of Federal Regulations (CFR), 1995 rev, Part 141, National Primary Drinking Water Regulations). The coliform group of organisms includes bacteria of the *Escherichia, Citrobacter, Klebsiella*, and *Enterobacter* genera. However, *Escherichia coli* is the specific organism indicative of fecal contamination, since the other members of the coliform family can be found naturally in the environment. Current water testing methods detect coliforms as a group so that positive results must be confirmed to be *E. coli* using additional methods. The slow turnaround time for traditional culture detection and confirmation methods (days) results in delays in detecting contamination as well as in determining when the water is safe for redistribution or use. Accordingly, there is a need for a rapid monitoring assay specific for *E. coli*.

Traditional methods for detecting coliform bacteria rely upon culturing on a medium that selectively permits the growth of gram-negative bacteria and differentially detects lactose-utilizing bacteria (Van Poucke, et al. *Appl. Environ. Microbol.* (1997) 63(2):771-4; Standard Methods for the Examination of Water and Wastewater, 19th ed., American Public Health Association, 1995). Since 1880, coliforms have been utilized as an indicator organism for monitoring the microbiological quality of drinking water. However, there are recognized deficiencies (Van Poucke, supra). This includes maintaining the viability of bacteria between the time of collection and enumeration, and the existence of chlorine stressed viable but non-culturable bacteria. False negatives can occur due to suppression of coliforms by high populations of other organisms or *E. coli* strains that are unable to ferment lactose (Edberg, et al. *Appl Environ Microbiol*. (1990) 56(2):366-9), and false positives occur due to other organisms that ferment lactose. Culture methods take 24-48 hours for initial coliform enumeration with an additional 24 hours for *E. coli* confirmation.

*Escherichia coli* is a member of the family Enterobacteriaceae and as such, shares much of its genomic sequence with other members of this family (Lampel, et al. *Mol. Gen Genet.* (1982) 186(1):82-6; Buvinger, et al. *J Bacteriol.* (1985) September; 163(3):850-7). For many purposes, it would be useful to specifically identify *E. coli* in the presence of other organisms, including members of the same family. However, because of the close conservation of sequence between *E. coli* and other Enterobacteria, amplification primers specific for *E. coli* are difficult to design.

Although there are gene-based methods described in the art for the detection of certain subsets of the coliform group, only a few of these claim to detect only *E. coli*. There are a number of studies that confirm coliform detection using uidA gene. Lupo et al. (*J. Bacteriol.* (1970) 103:382-386) detected uidA in 97.7% of 435 *E. coli* isolates, half from treated water and half from raw water. Graves and Swaminathan (Diagnostic Molecular Microbiology, (1993) Persing et. al., eds, ASM, p. 617-621) detected 100% of 83 confirmed environmental *E. coli* isolates using a uidA probe. Another study (Bej, et al. *Appl Environ Microbiol.* (1991) 57(4):1013-7) utilized uidA to detect 97% of 116 *E. coli* isolates. However, specificity studies investigating potentially cross-reactive organisms confirm that uidA probes detects both *E. coli* and some *Shigella* spp. (Bej, et al. (1991) supra; Green et. al., *J. Microbiol. Methods* (1991) 13:207-214; Rice et. al., *J. Environ. Sci. Health* A30:1059-1067, 1995).

Total coliforms can be detected using the lacZ gene that codes for beta-galactosidase (Bej, et al., *Appl. Environ. Microbiol.* (1990) 56(2):307-14; Bej, et al, *Appl. Environ. Microbiol.* (1991) 57(8):2429-32). Utilizing PCR amplification methods, Bej demonstrated limits of detection of 1-5 CFU in 100 ml of water. Atlas, et. al. disclose lacZ DNA sequences that identify coliform species of the genera *Escherichia, Enterobacter, Citrobacter*, and *Klebsiella* (U.S. Pat. No. 5,298,392).

Although Min and Baeumner (*Anal. Biochem.* (2002) 303:186-193) disclose sequences of the heat shock protein gene clpB, their publication only shows specificity compared to non-coliform genera and does not include cross-reaction data for other coliforms.

SUMMARY OF THE INVENTION

Accordingly, one aspect of this invention provides a method that permits the multiplex amplification of multiple targets without extensive design and optimization constraints. More specifically, this invention comprises a two-step multiplex amplification reaction wherein the first step truncates a standard multiplex amplification round thereby resulting in a product having a boosted target copy number while minimizing primer artifacts. The second step divides the resulting product achieved in the first step into optimized secondary single amplification reactions, each containing one of the primer sets that were used previously in the first step.

This invention further provides a method that enables amplification of multiple targets (or multiple amplification assays) from limited quantity specimens with very low nucleic acid copy number.

This invention further provides a diagnostic kit that allows the user to perform amplification of multiple targets without extensive design and optimization constraints and to amplify targets from limited quantity specimens with very low nucleic acid copy number.

This invention further discloses specific nucleic acid sequences that are unique to *E. coli* and which are located on the LacZ gene of *E. coli*. Accordingly, another aspect of this invention provides a method of detecting a single CFU of *E. coli*. More specifically, this invention provides a method of utilizing these specific sequences to detect 1 CFU of *E. coli* following NASBA amplification reactions without the need for long culture enrichment. This invention further includes a method of using IPTG induction to increase sensitivity in detecting the unique *E. coli* sequences disclosed herein.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE DRAWINGS

The accompanying drawings, which are incorporated in and form a part of the specification, illustrate the preferred embodiments of the present invention, and together with the description serves to explain the principles of the invention. In the Drawings.

DETAILED DESCRIPTION OF THE PREFERRED EMBODIMENT

Figure 1:
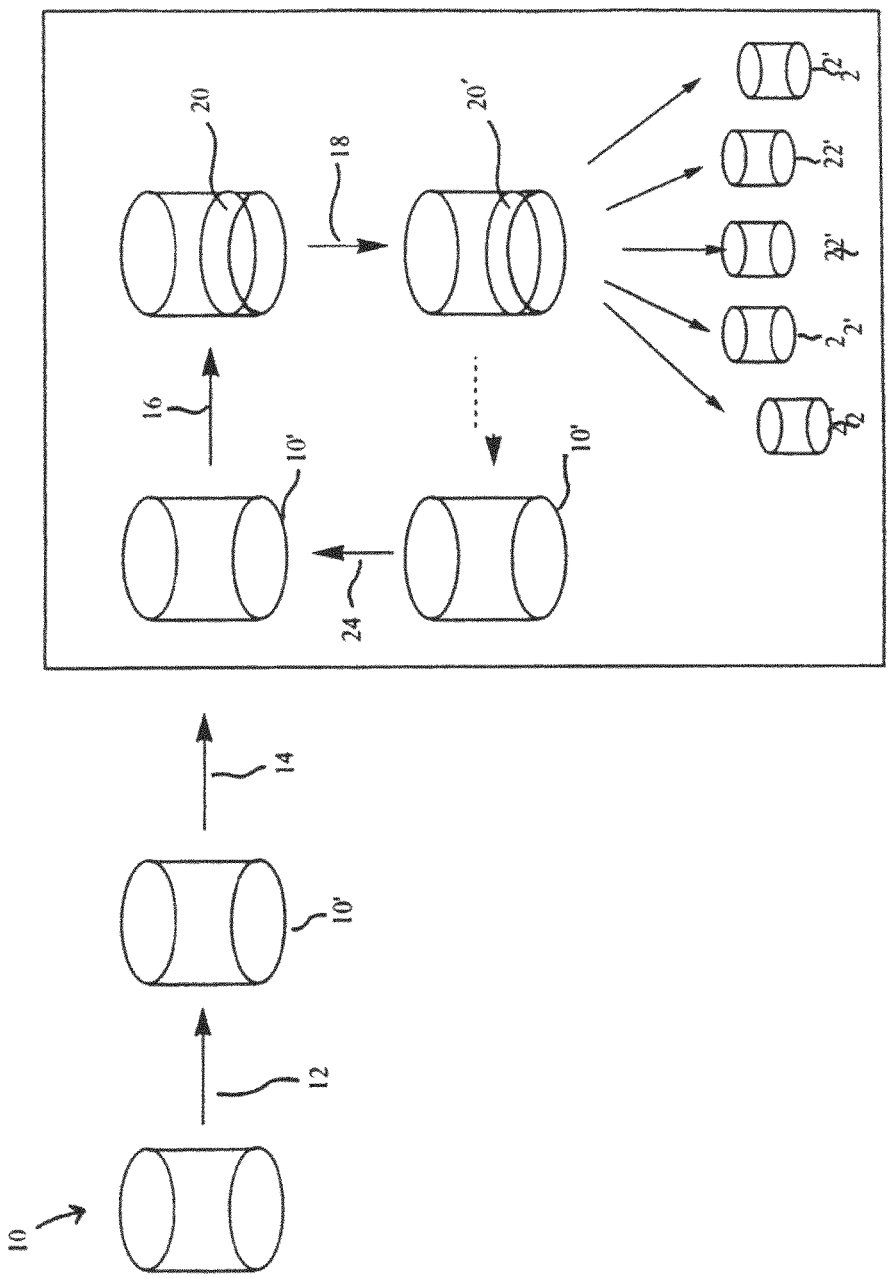
FIG. 1 is a diagrammatic illustration of the limited multiplex amplification method of the present invention.

As discussed above, it would be tremendously useful if a method and diagnostic kit could be devised to multiplex multiple nucleic acid targets without the necessity of complex design constraints and extensive optimizations. The methods and diagnostic kit of the present invention generally involve the use of common multiplex amplification methods and reagents and are more specifically derived from the surprising discovery that if the nucleic acid sample to be analyzed is first pre-amplified so as to merely "boost" the samples copy number slightly, then the resulting product may be split into as many subsequent analysis reactions as required, and thereby circumventing the common limitations of standard multiplexing technology.

The present invention describes a novel method for boosting the amount of nucleic acid obtained from a broad range of biological samples for distribution among large numbers of individual analyses. It preferably involves the utilization of archived nucleic acid, bound irreversibly to a solid-phase material as the starting material. See U.S. application Ser. No. 09/061,757 and corresponding international application WO 98/46797, each of which is specifically incorporated herein by reference. The copy number of the irreversibly bond nucleic acid is then "boosted" by running a limited multiplex amplification reaction. The limited multiplex amplification reaction is a truncated version of any well known amplification methods such as, but not limited to PCR, RT-PCR, NASBA, SDA, TMA, CRCA, Ligase Chain Reaction, etc. Using archived nucleic acid has the advantage that multiple sequential rounds of the present invention may be performed. Alternatively, nucleic acids that are not bound but in aqueous solution may also be used. In this instance nucleic acid is obtained from the desired biological sample by a number of common procedures. These include phenol-chloroform and/or ethanol precipitation (Maniatis, et al., Molecular Cloning; A Laboratory Manual), high salt precipitation (Dykes, *Electrophoresis* (1989) 9:359-368), chex and other boiling methods (Walsh, et al., *Biotechniques*, (1991) 10:506-513 and other solid phase binding and elution (Vogelstein and Gillespie, *Proc. Nat. Acad Sci. USA*, (1979) 76:615-619, etc. Output from these initial rounds of limited amplifications is distributed into the several single analyses.

As discussed above, it is desirable to be able to detect a single CFU of *E. coli*. Current methods for obtaining this level of sensitivity generally require culturing the organism overnight in order to reach detectable cell numbers. Both the lacZ beta-galactosidase (Bej, et al. *Appl Environ. Microbiol.* (1991) 57(8):2429-32; Sheridan, et al. *Appl. Environ. Microbiol.* (1998) 64:1313-1318) and the uidA beta glucuronidase enzymes (Vaitilingom, et al., *Appl. Environ. Microbiol.* (1998) 64:1157-1160; Berg and Fiksdal, *Appl. Environ. Microbiol.* (1988) 54:2118-2122; Tryland I, et al. *Appl. Environ. Microbiol.* (1998) 64(3):1018-23) have been shown to be readily inducible using environmental isolates. Lactose induction of membrane filter collected environmental isolates was shown to increase enzyme activity as much as 1000-fold resulting in detection limit of 100 CFU per 100 ml within 15 minutes of collection (Davies, et al., *Lett. Appl. Microbiol.* (1995) 21(2):99-102).

This invention provides a unique strategy to increase sensitivity by inducing the transcription of multiple mRNA copies within the *E. coli* cell in order to more rapidly reach detectable levels following NASBA amplification. Detection of a single CFU of *E. coli* is accomplished by diluting the bacteria suspended in water into an induction media with isopropyl β-D-thiogalactopyranoside (IPTG) and incubating for about 2-6 hours to allow for mRNA transcription as described in detail in Example 3. The cells are lysed and released RNA bound to Xtra Amp™ tubes using the package insert directions (see also U.S. Pat. No. 6,291,166, which is specifically incorporated herein by reference). The solid phase captured RNA is amplified directly using the *E. coli* target recognition sequences disclosed herein that have been modified for NASBA amplification and lateral flow detection as described in U.S. Pat. No. 5,989,813 and U.S. patent application Ser. No. 09/705,043, each of which are specifically incorporated herein by reference.

In one preferred embodiment of the present invention, a sample containing tissue, cells or other biological material is treated in the presence of the solid phase binding material to release the nucleic acid contained in that sample. The solid phase archiving material allows amplification without elution of the bond nucleic acid. Once the sample nucleic acid is bound to the solid phase, the solid phase material is washed to remove lysis buffer conditions, and to prepare for amplification conditions. A reaction mixture appropriate to the amplification method is added to the solid phase or allowed to contact the solid phase. The number of primer pairs used according to the present invention may be any number greater than two, however, since the standard multiplexing reaction conditions and designs become more difficult and less effective as the number of primers used increases the present invention is most helpful as the number of primers utilized is over five.

This reaction mixture contains the amplification primers for several independent amplifications. This is similar to standard multiplex PCR with the following exceptions: first, in the preferred embodiment, the primer concentrations will be very low. The effective primer concentrations should be limited to allow only a few logs of amplification but definitely the primer concentration should be exhausted before reaction plateau is reached. Second, the number of amplification cycles should also be minimized. The goal of this first phase of multiplex amplification or "Booster Amp" is to allow only a sufficient amount of amplification to proceed in order to allow the resultant reaction mix to be split up and redistributed into at least the same number of subsequent simples amplification reactions as there are independent primer pairs in the first amplification.

This initial round of amplification, or Booster Amp should only proceed into early logarithmic phase of the amplification, and in no instance proceed until reaction plateau is reached. Once the Booster Amp is complete, the resultant reaction mix with the multiple amplification species is removed from contact with the solid phase and distributed into several secondary amplifications. These amplifications could be equal to or greater than the number of primer pairs employed in the first Booster Amp. Each of these secondary amplification reactions will contain only one primer pair. This primer pair may be identical to one of the primer pairs in the Booster Amp or may be "nested" within one of the primer pairs of the Booster Amp. Either way, each secondary amplification reaction will use the input material from the Booster amplification as a target source. In the secondary amplification, normal amounts of primer will be used, and amplification will be allowed to proceed normally. A detection system for normal detection of a single amplification product such as, but not limited to radioactive isotopes, or visual markers such as biotin may be included in the secondary amplification.

In the preferred embodiment the reaction takes place in the presence of a solid phase material as discussed previously. The advantage of this is that the original solid phase material with the bond nucleic acid may be rinsed following the first Booster Amp and re-initialized for a second, subsequent Booster Amp employing a new mix of amplification primers. The process is then repeated through an additional secondary amplification. The entire process can be repeated for numerous rounds. Consequently, in the event the quantity of nucleic acid sample being analyzed is low, the analysis may be performed as often and as thoroughly as need be. Alternatively, the Booster Amp step may be performed in aqueous condition where the nucleic acid is unbound.

FIG. 1 illustrates the concept for microwell based PCR (but can apply to any primer-based amplification method utilizing a polymerase, such as but not limited to DNA polymerase, RNA polymerase, transcriptase, or Qβ replicase in any form of an appropriate container). A chip or card containing the reaction wells or chambers (not shown) is contained in a device capable of performing the correct thermocycling. Lysed sample is introduced into extraction chamber 10, where the freed nucleic acid can bind to the solid phase material within extraction chamber 10. The chamber 10 having bound the sample is incubated is step 12 for a short period (10-20 minutes). An aqueous buffer, preferably PCR buffer is then used in washing step 14. The wash 14 removes lysate and initializes the chamber 10' in step 16 for PCR conditions. The first multiplex PCR reaction mixture (containing multiplexed primers, PCR buffer, and Taq Polymerase) is introduced to the chamber 10 and cycled in step 18. The multiplex products 20' should be sub-detectable, but amplified to a level no greater than the plateau of the reaction and preferably in the range of 100 to 1000-fold. The Booster PCR reaction 20' is then split into the secondary PCR chambers 22'. Reaction mixtures (having a single primer pair) for each of the simplex, secondary PCR reactions (not shown) are introduced previously, or at this point. Cycling is performed on the chip or card to allow the secondary PCR reactions 22' to proceed to completion. The initial sample chamber is now empty, and it can be washed at step 24 and re-initialized for a second round of Booster/Secondary PCRs.

This invention includes nucleic acid sequences that are substantially homologous to the SEQ ID NO. 99. By substantially homologous it is meant a degree of primary sequence homology in excess of 70%, most preferably in excess of 80%.

This invention reveals a robust and simple method for multiplex amplification of large numbers of gene targets. The invention teaches that preferably 2-40 or more primer sets can be combined to permit multiplex amplification if they are in low concentration and limited to an initial amplification round that results in only a 100-1000 fold increase in target. However, it should be understood that any number of primer sets greater than two may be used according to the present invention. This has been designated as a "booster round" or booster amp and can occur using an aqueous target nucleic acid or using solid phase archived nucleic acid. As discussed above, the advantage of using archived material is that multiple booster rounds can be performed from the same archived specimen. For example, performing five, 20-target booster rounds from archived nucleic acid would permit the analysis of 100 different genes. Following each booster round the amplification product is diluted into optimized secondary single PCR reactions, each containing one of the primer sets that were multiplexed in the booster reaction. These simplex reactions can be optimized for maximum sensitivity and each requires only one method of detection, for example single dye homogeneous detection. The invention enables multiplexing without extensive optimization and is robust enough to permit random selection of the primers to be multiplexed.

The invention overcomes the usual technical problems of multiplexing. By limiting the multiplexed cycles, preferential amplification and cross-reaction of the multiple primers is minimized. Only the single PCR reactions need to be optimized. The simplex reaction has maximum sensitivity since reagent competition does not occur. By using the simplex PCR the detection probe does not have to be multiplexed. The potential to randomly combine the multiplexed primers provides for maximum flexibility and cost effectiveness since this allows custom selection of the targets to be multiplexed. Frequently, the targets that need to be multiplexed can vary for a particular geographic location, laboratory, type of patient, or type of specimen. Since archived nucleic acid can be reanalyzed the multiplex can be designed in a logical algorithm. For example, in booster reaction detection set number one, identify the most frequently known mutations. Then only if these are not detected is it necessary to perform additional multiplexes for the more rare mutations. This enables economical yet comprehensive genetic analysis.

The invention is further illustrated by the following non-limited examples. All scientific and technical terms have the meanings as understood by one of ordinary skill in the art. The specific examples which follow illustrate the various multiplexing amplification methods that the present invention may be adapted to work with and are not to be construed as limiting the invention in sphere or scope. The methods may be adapted to variation in order to function with other commonly used multiplex amplification methods embraced by this invention but not specifically disclosed. Further, variations to the methods to produce the same results in somewhat different fashion will be evident to one skilled in the art.

All temperatures are understood to be in degrees Centigrade (° C.) when not specified. Melting temperatures (Tm) of the primers were estimated using the generally accepted mathematical calculation based upon the formula Tm=81.5+ 16.6×log (Na$^+$) (41×(#G+#C)/length)−500/length. Amplification techniques, including multiplexing amplification techniques, are now sufficiently well known and widespread so as to be considered routine. All polymerase enzymes and nucleotides can be purchased from PE (Biosystems, Foster City, Calif.). PCR was carried out in a buffer containing (50 mM KCl, 10 mM Tris, pH 8.3, 2.0 mM Mg$^{2+}$) for 30 cycles of 1 minute at 94° C., for 2 minutes at 55° C. and at 72° C. with a 5 second increment added to the 72° C. elongation step at every cycle. This procedure was carried out in a DNA Thermal Cycler (Perkin-Elmer Cetus catalog No. N8010150).

Example 1

Multiplex Amplification Incorporating Booster PCR and Archiving.

1. Primer Design:

The Xtra Amp™ Extraction Kit (Xtrana, Inc.) provides an innovative system for nucleic acid extraction in which the nucleic acid remains bound in the extraction tube and can be directly amplified by PCR in this same tube. The unique principle underlying this system lies in the proprietary nucleic acid binding matrix, Xtra Bind™. Xtra Bind™ is a non-silica matrix which stably and irreversibly binds both DNA and RNA. The Xtra Amp™ kit contains 96 (as 1×8 strips) 0.2 mL size microcentrifuge tubes coated with the Xtra Bind™ matrix, cell lysis buffer and wash buffer. The kit is commercially available currently for extraction of genomic DNA from, whole blood (manufactured and distributed for Xtrana, Inc. by ANSYS Diagnostics, Lake Forest, Calif.). For demonstrating Xtra Plex feasibility, the Xtra Amp™ Blood kit was chosen as the extraction platform. For the PCR multiplexing experiments it was decided to obtain twenty five primer pairs to allow their use in various groupings. Three primer sets from the Lifecodes Corporation (Stanford, Conn.) HLA Primers (HLA-A: Primer A1 (catalog No. 164011); Primer A2 (catalog No. 164012); HLA-B: Primer B1 (catalog No. 165011), Primer B2 (catalog No. 165012; DRβ: Primer A (catalog No. 160031); Primer B (catalog No. 160032) were added to twenty three in-house primer sets, shown below in Table 1, that were designed for human gene targets to make the total of twenty five sets. The genes targeted are as follows: Human cytoplasmic beta-actin gene (accession M10277); *Homo sapiens* interleukin 2 precursor (IL2) gene (accession J00264); Human growth hormone gene (HGH-N) (accession M13438); Human glyceraldehyde-3-phosphate dehydrogenase (GAPDH) gene (accession J04038); *Homo sapiens* dystrophin (DMD) gene (accession AF214530); *Homo sapiens* G protein-coupled receptor 57 (GPR57) gene (accession AF112461); Human galactokinase (GALK1) gene (accession L76927); *Homo sapiens* MHC class 1 region (accession AF055066). The primer pairs were designed using the primer design software OLIGO 5.0 (Molecular Biology Insights). The sizes of the amplification products are designed to allow discrimination by agarose gel electrophoresis. No special considerations were given to normalizing the melting temperatures of the primer pairs, or to eliminating structural interactions between primers from different pairs. PCR primer design considerations such as avoiding hairpins and dimers between the forward and reverse primers of each set were accommodated in the design as for any typical PCR primer design. The resultant primers had melting temperatures ranging from 49° C. to 72° C. When examining the dimer formation potential between primers from different pairs, some serious dimer potential was seen in some cases. This was largely ignored since this approach was believed to be able to overcome such potential artifacts and it was considered important to demonstrate this. The primers and sequences are shown in Table 1.

TABLE 1

| Primer Pair | SEQ ID NO: | Sequence | Name | TM | Amplicon Length |
|---|---|---|---|---|---|
| *Group 1* | | | | | |
| 1 | 1 | CGAGGCCCAGAGCAA | HBAPCR1-FP | 58 | 100 |
|   | 2 | GGTGTGGTGCCAGATTT | HBAPCR1-RP | 57 | 100 |
| 2 | 3 | GTTTAATCAGAGCCACA | IL2 = PCR2-FP | 52 | 187 |
|   | 4 | GGAAAGGTAGGTCAAGA | IL2 PCR2-RP | 54 | 187 |
| 3 | 5 | GTCTTGCATTGCACTAA | IL2-OLD-fp | 52 | 257 |
|   | 6 | TAAATGTGAGCATCCTG | IL2-OLD-rp | 52 | 257 |
| 4 | 7 | CTGTGGAGGGCAGCTGTGGCTT | hGH PCR1-FP | 68 | 450 |
|   | 8 | GCGGGCGGATTACCTGAGGTCA | hGH PCRI-RP | 68 | 450 |
| 5 |   | Lifecodes HLA-A, A1 | HLA-A-A1 | N/A | 910 |
|   |   | Lifecodes HLA-A, A2 | HLA-A-A2 | N/A | 910 |
| *Group 2* | | | | | |
| 6 | 9 | TCAGCAGAGAAGCCTAA | IL2-PCR1-RP | 54 | 120 |
|   | 10 | ATCCCTACCCCATCAT | IL2-PCR1-FP | 54 | 120 |
| 7 | 11 | CAAAAGTCCTCCCAAAG | IL2-PCR3-RP | 54 | 197 |
|   | 12 | TGCCATCTATCACAATCC | IL2-PCR3-FP | 55 | 197 |
| 8 | 13 | AAGGGTCATCATCTCTGC | GAPDH 15 fp | 57 | 259 |
|   | 14 | CTTCCACGATACCAAAGTT | GAPDH 15 rp | 55 | 259 |
| 9 | 15 | CGCTTTAAGTTATTTGTGTC | HDYST3-FP | 54 | 400 |
|   | 16 | GTTTCCTTTTAAGGGTATTC | HDYST3-RP | 54 | 400 |
| 10 |   | Lifecodes HLA-B, B1 | HLA-B-B1 | N/A | 1100 |
|   |   | Lifecodes HLA-B, B2 | HLA-B-B2 | N/A | 1100 |
| *Group 3* | | | | | |
| 11 | 17 | CATCTACGAGGGGTATG | HBAPCR2-FP | 57 | 120 |
|   | 18 | GCCGTGGTGGTGA | HBAPCR2-RP | 54 | 120 |
| 12 | 19 | GTTTGCCTTTTATGGTAATAAC | HBAPCR4-FP | 55 | 161 |
|   | 20 | GTGAGCTGCGAGAA | HBAPCR4-RP | 54 | 161 |
| 13 | 21 | GAGTCCACTGGCGTCTTCAC | GAPDH FP | 64 | 233 |
|   | 22 | AGGCTGTTGTCATACTTCTC | GAPDH RP | 58 | 233 |
| 14 | 23 | CCACCCCCTTAAAGAAA | IL2-PCR4-RP | 54 | 346 |
|   | 24 | GGCAGGAGTTGAGGTTA | IL2-PCR4-FP | 57 | 346 |
| 15 | 25 | GCGGGGAGGAGGAAAGGAATAG | hGHPCR2-FP | 66 | 500 |
|   | 26 | CAGGACACATTGTGCCAAAGGG | hGHPCR2-RP | 64 | 500 |
| *Group 4* | | | | | |
| 16 | 27 | CCACTATTCGGAAACTT | HGP57R1-FP | 52 | 130 |
|   | 28 | TGTATGGCATAATGACA | HGP57R1-RP | 49 | 130 |
| 17 | 29 | GAGTCGAGGGATGGCTAGGT | HDYST1-FP | 64 | 150 |
|   | 30 | TTCAAAGTGGGATGAGGAGG | HDYST1-RP | 60 | 150 |
| 18 | 31 | GGACTGCCACCTTCTACC | HGKPCR1-FP | 62 | 215 |
|   | 32 | GACACCCAAGCATACACC | HGKPCR1-RP | 59 | 215 |
| 19 | 33 | GCAGATGAGCATACGCTGAGTG | hGHPCR3-FP | 64 | 600 |
|   | 34 | CGAGGGGAAATGAAGAATACGG | hGHPCR3-RP | 62 | 600 |
| 20 |   | Lifecodes DR-β, A | DR-β, A | N/A | 287 |
|   |   | Lifecodes DR-β, B | DR-β, B | N/A | 287 |
| *Group 5* | | | | | |
| 21 | 35 | AGGGGAGGTGATAGCAT | HBAPCR3-FP | 57 | 140 |
|   | 36 | AAGTTGGGGACAAAA | HBAPCR3-RP | 51 | 140 |
| 22 | 37 | CCGGTGCCATCTTCCATA | HGKPCR1-FP | 68 | 170 |
|   | 38 | CCTGCCTTGCCCATTCTT | HGKPCR1-RP | 68 | 170 |
| 23 | 39 | GAGGGGAGGAGGGGTAA | HBAPCR5-FP | 62 | 228 |
|   | 40 | CGGCGGGTGTGGA | HBAPCR5-RP | 57 | 228 |
| 24 | 41 | GGCTGCTTTTAACTCTGG | GAPDH FP | 57 | 270 |
|   | 42 | CACTCCTGGAAGATGGTGATGG | GAPDH RP | 64 | 270 |
| 25 | 43 | CTCATTCTCTAGCCAAATCT | HDYST2-FP | 56 | 300 |
|   | 44 | CCTCGACTCACTCTCCTC | HDYST2-RP | 62 | 300 |

TABLE 1 -continued

| SEQ ID NO: | Sequence | Name | TM | Amplicon Length |
|---|---|---|---|---|
| New Primers | | | | |
| 26 | 45 CTATCGCCATCTAAGCCCAGTA | HGH PCR4-fp | 62 | 450 |
| | 46 CTGCCTGCATTTTCACTTCA | HGH PCR4-Rp | 58 | 450 |

2. Sequential Booster Reaction of Solid-Phase Captured Nucleic Acid.

In these multiplexing experiments, (the results of which are demonstrated in FIGS. 2a-2d) designed to show feasibility for performing multiple rounds of multiplexing amplification, each booster amplification consisted of a PCR reaction with five primer sets. In the first 5-plex experiment, Group 2 primers were used. In the second experiment group 4 primers were used, and in the third, group 1 primers were used. In the 20-plex experiment, the primers used were selected from all 5 groups each at one-fiftieth normal concentration (4 nM as opposed to 200 nM). The nucleotide triphosphate, buffer and salt concentrations were normal. Cycling conditions were chosen as a compromise between the theoretically optimal conditions for each of the primer pairs (each cycle: 72° C., 30 seconds; 55° C., 1 minute; and 65° C., 3 minutes). The total number of cycles was limited to ten. The primers were first mixed in 1:1 ratios to each and then diluted to one-fiftieth of the normal 10× concentration. The PCR reaction mix for the booster reaction was made up as per normal. The Xtra Amp™ kit (discussed previously) was used with fresh human blood as per the kit protocol. The booster reactions were placed into the Xtra Amp™ tubes as would a normal PCR. Following the booster PCR, the reaction mixture was removed and diluted 5-fold.

To each simplex, secondary reaction 5 microliters of this diluted booster product was added. Each secondary reaction had only one of the 5 primer pairs and was set up normally with normal amounts of primer. These PCRs were run for the full 40 cycles. Two cycling profiles (72° C., 30 seconds; 65° C., or 1 minute; 72° C., 3 minutes) were used for these secondary reactions. The same cycling profile used in the booster reactions was used for all secondary PCRs. In cases where the primers were believed to require higher temperatures, additional secondary reactions were run using higher temperature profiles (each cycle: 72° C., 30 seconds; 65° C., 1 minute; 72° C., 3 minutes).

Next, the Xtra Amp™ tube in which the booster reaction was performed was rinsed three times with Wash Buffer supplied in the kit. A second booster PCR reaction mixture with a different set of five primer pairs was added to the tube. Identical conditions were used as in the first booster amplification. The product was removed and diluted as before, and aliquoted into the next group of five secondary, simplex PCRs using the same primer pairs as in the second booster PCR. All of these secondary reactions were run using the same cycling profile as the booster, with some primers being additionally run at the higher temp profile as well. Following this, a third round of booster/secondary simplex reactions were run with a third grouping of five primers in identical conditions to the first two rounds.

For comparison, a normal, 40-cycle multiplex PCR was run using each of the five primer pair groupings. Each of these had five primer pairs each in the same groupings as the booster PCRs. These multiplex reactions were run with half-normal primer concentration for 40 cycles. The products from all fifteen secondary reactions, the high-temp additional secondary reactions and the three normal multiplexing PCRs were analyzed by agarose gel electrophoresis.

Figure 2A:
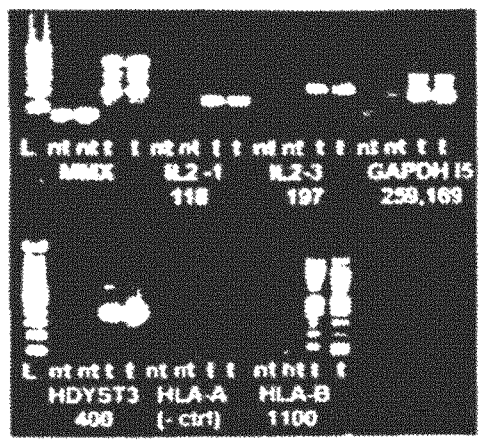
FIG. 2A is an illustration of an agarose gel showing the results of the experiment in Examples 1 and 2.

FIG. 2A demonstrates the results of the first round of the secondary PCR reactions. Five PCRs were used in first round (Group 2: IL2-1; IL2-3; GAPDH 15; HDYST3; HLA-B) booster PCR. The Booster PCR was performed in an Xtra Amp™ tube following extraction of nucleic acids from human blood. Following booster amplification, product was diluted 1:5, then 1:10 volume of this was added to six subsequent reactions in separate normal PCR tubes. The six subsequent simplex secondary reactions included all five of the Booster PCR systems, with an additional system (HLA-A) whose primers were similar to one of the five (HLA-B). The additional PCR served as a secondary PCR control and was expected to be negative. The results shown in FIG. 2A demonstrate that all five PCRs from Booster worked in the secondary simplex reactions. In contrast, a normal multiplex PCR (MMX) in which all five primer pairs were run in a similarly prepared Xtra Amp™ tube for a total of 40 cycles did not work for all PCR products. (In this and all gel images pictured, the reference ladder is in 100 base-pair increments starting at 100 bp L is ladder, nt is no template and t is template).

Figure 2B:
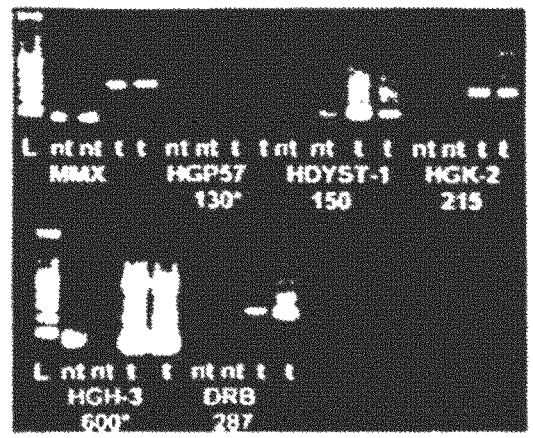
FIG. 2B is an illustration of an agarose gel showing the results of the experiment in Examples 1 and 2.

FIG. 2B demonstrates the results of the second round of the secondary PCR reaction. The second round of 5-primer pair booster PCR was run in the same Xtra Amp™ tube as was the first booster. The tube was washed three times with Xtra Amp™ kit wash buffer prior to the addition of the second booster multiplex PCR mix. The next five primer pairs were from Group 4: HGP57; HDYST-1; HGK-2; HGH-3, and DRB. Following an identically run booster PCR, the product was diluted 1:5 as before and aliquoted into the five secondary simplex PCR reactions. These reactions were run at the low temperature cycling range. The results shown in FIG. 2B demonstrates that the four reactions worked at this temperature with some spot contamination in one of the HDYST-1 no-template controls. The HGP57 and HGH-3 secondary reactions work best at the high temperature secondary cycling protocol and were done at that temperature as well. A normal PCR multiplex (MMX) with these same primers in an Xtra Amp™ tube failed again.

Figure 2C:
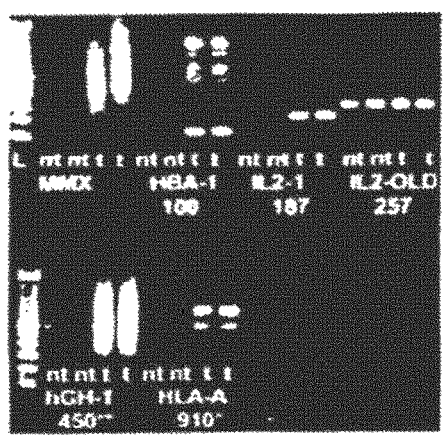
FIG. 2C is an illustration of an agarose gel showing the results of the experiment in Examples 1 and 2.

FIG. 2C demonstrates the results of the third round of the secondary PCR reactions. In this experiment, a third 5-primer pair booster multiplex was performed in the same Xtra Amp™ tube as was the first two booster reactions, discussed above, using primer sets from group 1 (HBA PCR 1; IL2 PCR 2; IL2 PCR-old; hGH PCR 1 and HLA-A). Again, three standard washes were done with the tube between the previous booster PCR and this one. The standard 40-cycle multiplex with these primers failed with these primers as well. The results shown in FIG. 2C demonstrates that some contamination in the no template controls was seen in the IL2-OLD primer reaction, and the hGH-1 PCR did not work well with the low temperature cycling condition set for the secondary reactions. Both the hGH-1 and HLA-A secondary reactions were run at the high temperature secondary cycling condition set (65° C. and 72° C. vs. 55° C. and 65° C.).

Figure 2D:
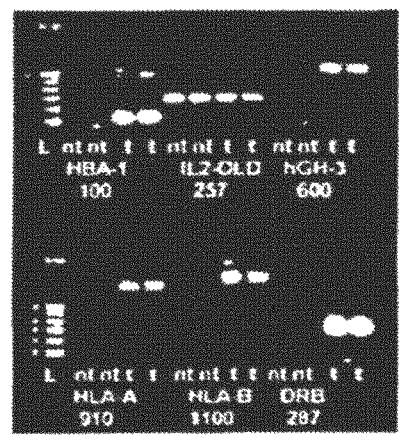
FIG. 2D is an illustration of an agarose gel showing the results of the experiment in Examples 1 and 2.

The results shown in FIG. 2D demonstrates that in this set of secondary reactions, the primer sets which appeared to be compromised in the first sets of secondary reactions were rerun using higher annealing and extension temperatures (65° C. and 72° C. vs. 55° C. and 65° C., respectively). The contamination issue with IL2-OLD was still apparent (this primer set had been used previously in our lab). The remaining PCR reactions were much more robust.

The results indicate that all of the secondary reactions worked. In one case where a primer pair had been used extensively in this lab prior to these experiments (IL2-OLD) there appeared some contamination in the no template controls. One primer pair gave weak positive results (HGP-57). Four primer pairs worked better at the higher temperature secondary PCR profile. One primer pair worked better at higher concentration in the secondary reaction. These results indicate that the secondary PCR reactions function as normal PCR reactions in which some optimization will give better results. The booster PCR was able to function adequately at less than optimal conditions for the various primer sets. In contrast, the three normal multiplex PCRs that were run as multiplex amplifications for the full 40 cycles failed to show amplification products for all but a few primer sets.

Figure 3:
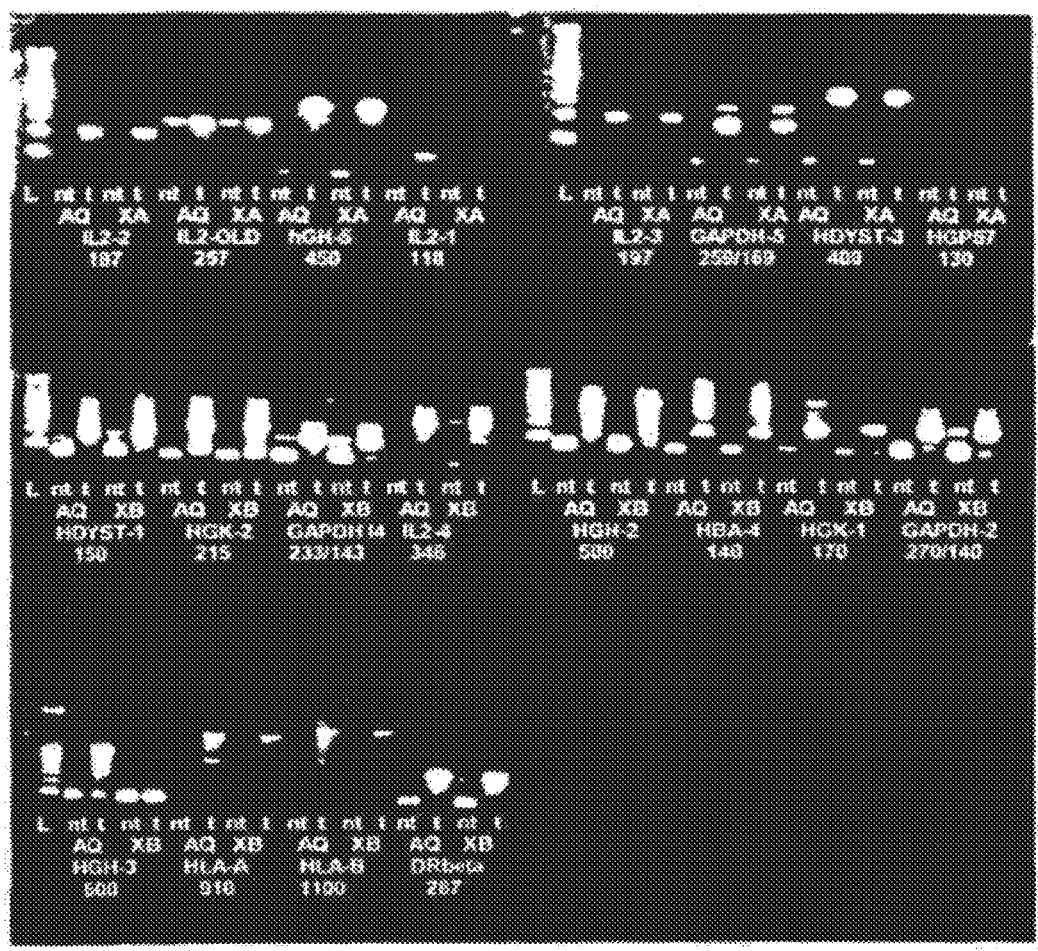
FIG. 3 is an illustration of an agarose gel showing the results of the experiment in Example 1-3.

3. Multiplex Capability Enabled by Booster PCR:

Since the two-step PCR approach in which a limited-booster PCR is used to boost the target copy prior to aliquoting the boosted product into the individual secondary PCRs worked so well with groups of 5 primer pairs, increasing the number of primer pairs in the booster reaction was performed. A 20-primer pair booster reaction was set up using identical conditions as before, except that in addition to using the Xtra Amp™ kit with human blood as the sample, a booster PCR was set up in a normal PCR tube using previously extracted human placental DNA as the template. The primer set 23 replaced primer set 4 in this experiment. The individual primers were at 4 nM or one-fiftieth of normal concentration. The booster PCR was run for 10 cycles using the lower temperature profile (each cycle: 72° C., 30 seconds; 55° C., 1 minute; 65° C., 3 minutes). The product for this booster reaction was diluted 5-fold and used as template for the 20 secondary, simplex PCR reactions. The products from these reactions were analyzed by agarose gel electrophoresis as shown in FIG. 3. Although the contrast of the pictures obscures the results in some cases, all reactions gave product at the expected sizes for the aqueous PCRs. In some instances the aqueous reactions gave slightly better results than was seen for the reactions whose booster PCR was done in Xtra Amp™ tubes. Further optimization of the secondary reactions should eliminate those differences. The last four reactions (HGH-3, HLA-A, HLA-B and DRβ were done using the high temperature cycling condition set in the secondary reactions).

The results showed that all of the secondary PCRs from the aqueous (non-Xtra Amp) booster worked. Some of the secondary PCRs still need some minor optimization in order to yield cleaner products, but correctly sized product bands were seen for all reactions. Three secondary reactions from the Xtra Amp™ booster showed very weak product (poorly reproduced on gel photo). Additional optimization of the secondary reactions should improve the performance. It is noteworthy that even with 40 different primers being present in the booster PCRs, the secondary reactions worked yielding products of the correct size. This indicates that primer-primer artifacts across primer systems that may form in the booster reaction, and would most certainly form in a traditional one-step multiplex, do not interfere significantly with the secondary simplex reactions.

By performing the two-step multiplex of multiplex booster followed by simplex secondary reactions, large numbers of assays can be done with a single sample without encountering the confounds associated with normal single-step multiplex amplification. Of further note is the fact that, even when using PCR primers that have not been optimized in any way and boosting with a profile that is demonstrably less than optimal for at least some of the primer sets used, the approach is still robust.

Example 2

Sequential Booster Xtra Plex NASBA Reaction of Solid-Phase Captured Nucleic Acid 1. Booster Xtra Plex NASBA First Pass Several NASBA systems are currently in operation in our lab. From these, ten primer sets as shown in Table 2 were chosen. These were: (1) for *Escherichia coli*: SZ gene (SZ), SLT1 and 2 genes (SLT1, SLT2), 16S ribosomal RNA (16S), LacZ (LacZ 1 and LacZ 2), and UIDA gene (UIDA); (2) for *Listeria monocytogenes*: HlyA gene; (3) for *Nisseria gonorrhea*: 16s ribosomal RNA (NG2); and (4) for *Chlamydia trachomatis*: 16s ribosomal RNA (CT2). Surprisingly, the primers LACZ 1 and LACZ 2 have been shown to be specific to *E. coli* and can discriminate *E. coli* from other coliform species. The 16s ribosomal (16s) primer set is capable of binding to and allowing amplification of all gram-negative bacteria examined and may be a universal primer set for all gram-negative bacteria.

TABLE 2

| ORGANISM | SEQ ID NO: | GENE$^a$ | SEQUENCE |
| --- | --- | --- | --- |
| C. trachomatis | 47 | CT2: FP | AATTCTAATACGACTCACTATAGGGAGAGG TAACCGAAAGGTCCTAAGAT |
|  | 48 | CT2: RP | ATTGTTTAGTGGCGGAAGGG |
|  | 49 | CT2: 5DP | FITC-ACTTGGGAATAACGGTTGGAAA-PO$_4$ |
|  | 50 | CT2: 3DP | GCTAATACCGAATGTGGCGATA-Biotin |
| N. gonorrhea | 51 | NG2: FP | AATTCTAATACGACTCACTATAGGGAGAAC TGACATCGTTTAGGGCGTGG |
|  | 52 | NG2: RP | AATGCGTAGAGATGTGGAGG |
|  | 53 | NG2: 5DP | FITC-AGCCTCCTGGGATAACACTGACG-PO$_4$ |
|  | 54 | NG2: 3DP | AGCGTGGGTAGCAAACAGGATTAGA-Biotin |

TABLE 2 -continued

| ORGANISM | SEQ ID NO: | GENE[a] | SEQUENCE |
|---|---|---|---|
| E. coli | 55 | LacZ 1: FP | AATTCTAATACGACTCACTATAGGGAGAGG AAACTGCTGCTGGTGTTTTGCTT |
|  | 56 | LacZ 1: RP | TTACGGCGGTGATTTTGGCGAT |
|  | 57 | LacZ 1: 5DP | FITC-ATCGCCAGTTCTGTATGA-PO$_4$ |
|  | 58 | LacZ 1: 3DP | CCGACCGCACGCCGCATCCAGC-Biotin |
| E. coli | 59 | LacZ 2: FP | ATTCTAATACGACTCACTATAGGGAGAGGA GAACTGGAAAAACTGCTGCTGG |
|  | 60 | LacZ 2: RP | CGTTTACAGGGCGGCTTCGTCT |
|  | 61 | LacZ 2: 5 DP | FITC-ATCGCCAGTTCTGTATGA-PO$_4$ |
|  | 62 | LacZ 2: 3DP | CCGACCGCACGCCGCATCCAGC-Biotin |
| Coliform Bacteria | 63 | UIDA: FP | AATTCTAATACGACTCACTATAGGGAGA GGAATAGTCTGCCAGTTCAGTTCGTTGT |
|  | 64 | UIDA: RP | CAAAGTGTGGGTCAATAATCAGGAA |
|  | 65 | UIDA: 5DP | FITC-CTATACGCCATTTGAAGCCGAT-PO$_4$ |
|  | 66 | UIDA: 3DP | GTCACGCCGTATGTTATTGCCG-Biotin |
| E. coil 0157:H7 | 67 | SZ: FP | TTGTTAGCGTTACGTTTCCCTCT |
|  | 68 | SZ: RP | AATTCTAATACGACTCACTATAGGGAGAG GATAATACCAAATCAGGTTTTCCATTGA |
|  | 69 | SZ: 5DP | FITC-CGATGATGCTACCCCTGAAAAACT-PO$_4$ |
|  | 70 | SZ: 3DP | GAGAATGAAATAGAAGTCGTTGTT-Biotin |
| E. coil 0157:H7 | 71 | SLT 1: FP | GTTTGCAGTTGATGTCAGAGG |
|  | 72 | SLT 1: RP | ATTCTAATACGACTCACTATAGGGAGAGGAA CGTGGTATAGCTACTGTC |
|  | 73 | SLT 1: 5DP | FITC-ATCTACGGCTTATTGTTGAACGAAA-PO$_4$ |
|  | 74 | SLT 1: 3DP | TTTTATCGCTTTGCTGATTTTTCAC-Biotin |
| E. coil | 75 | SLT 2: FP | TTGCTGTGGATATACGAGGG |
|  | 76 | SLT 2: RP | ATTCTAATACGACTCACTATAGGGAGAGGAGAG TGGTATAACTGCTGTC |
|  | 77 | SLT 2: 5DP | FITC-TTTTGACCATCTTCGTCTGATTATT-PO$_4$ |
|  | 78 | SLT 2: 3DP | GTTAATACGGCAACAAATACTTTCT-Biotin |
| Universal | 79 | 16S: FP | AATTCTAATACGACTCACTATAGGGAGAGGACC TTGTTACGACTTCACCCCAG |
|  | 80 | 16S: RP | TACACACCGCCCGTCACACCAT |
| L. monocytogenes | 81 | HlyA: FP | AATTCTAATACGACTCACTATAGGGAGAACCTTT TCTTGGCGGCACA |
|  | 82 | HlyA: RP | GTCCTAAGACGCCAATCGAA |
|  | 83 | HlyA: 5DP | FITC-AACACGCTGATGAAATCTATAAGTATA-PO$_4$ |
|  | 84 | HlyA: 3DP | GTATTAGTATACCACGGAGATGCAGTG-Biotin |

[a]primer and probe sequences for NASBA (FP = forward primer, RP = reverse primer, 5DP = 5'-lateral flow detection probe, and 3DP = 3'-lateral flow detection probe)

Various cell extracts and artificial RNA templates were pooled (extracted RNAs, RNA runoff material, and RNA product from previous NASBA reactions). Twenty microliters of each were combined then diluted 1:1 with water. Thirty microliters of this mix was added to Xtra Amp™ tubes. To this was then added an equal volume of 2× LiCl lysis buffer. The solution was mixed and let sit for 20 minutes at room temperature. After 3 washes with LiCl wash buffer, the tubes were ready for NASBA.

Two sequential booster groups of 5 primer pairs each were then run in tandem. The booster NASBA reactions were run with normal reaction components and concentrations except that the primers were pooled and run at one-fiftieth of normal concentration (4 nM instead of 200 nM). Two booster reactions were set up in parallel and run for different times. The first was run for 15 minutes at 40° C., and the second for 30 minutes at 40° C. The reactions were terminated and the products removed from the tubes. The tubes were washed for the next round. The products were diluted 10-fold and used as template for the subsequent secondary simplex reactions. These reactions were run normally and analyzed by agarose gel electrophoresis and lateral flow where possible. The second group of five primer sets was then run identically in the same Xtra Amp™ tubes as were used in the first group booster. The procedure from booster to secondary simplex amplifications was identical. The groupings of the primer pairs were as follows: Group 1: SZ, SLT2, HlyA, CT2, and LacZ; Group 2: SLT1, 16S, NG2, LacZ1, and UIDA1.

The results indicated that four of the five secondary reactions from the first booster reaction worked as indicated either by agarose gel electrophoresis or lateral flow detection. The system that failed, E. coli SLT-2, is a system that has a history of inconsistent performance in our laboratory. All five of the secondary reactions from the second booster reaction worked. The gel results and lateral flow (Gerdes, U.S. Pat. No. 5,989,813 incorporated herein by references) results varied slightly. This variance has been seen with these systems previously and is indicative of sub-optimal conditions. Thus, although the reaction conditions require further optimization for full performance in the Booster Xtra Plex paradigm, the results are extremely encouraging and noteworthy in that they were so positive with completely untested and highly preliminary conditions.

2. Multiplex Capability Enabled by Booster NASBA:

Multiplexing isothermal amplification reactions is even more difficult than multiplexing PCR reactions. However there are applications in which an isothermal amplification of multiple targets would be the method of choice if that were possible. By employing the booster strategy developed for PCR but with NASBA primers this has been accomplished. A short booster NASBA reaction in which the ten primer pairs targeting genes products from diverse organisms was performed as above, but with all ten present in the same reaction. The booster NASBA was run with the HlyA NASBA condition set using 1:50 diluted primer mix per set (4.0 nM final concentration per primer). Template materials (extracted RNAs, RNA runoff material, and RNA product from previous NASBA reactions) for each primer set were pooled and diluted and used as template for the booster reaction. The template material was bound onto the Xtra Bind material in an Xtra Amp™ tube as above. This reaction was run at 40° C. for 15 minutes and 30 minutes. The products from these reactions were diluted ten-fold and used as template for the ten separate, secondary simplex NASBA reactions.

The results of the sequential booster Xtra Plex NASBA reaction of solid-phase captured nucleic acid, shown in Table 3, indicate that eight of the ten NASBA systems worked. One of the failures was the same system as in the above experiment. Again, the results are noteworthy in that at the time of this writing, even multiplexing two distinct primer sets in a NASBA reaction has not been demonstrated.

TABLE 3

Sequential Booster Xtra Plex NASBA Reaction of Solid-Phase Captured Nucleic Acid Results

| Primer Pair | Agarose Gel Results | Lateral Flow Results |
|---|---|---|
| Group 1: | | |
| E. coli SZ | Negative | Positive |
| E. coli SLT 2 | Negative | N/A |
| L. monocytogenes HlyA | Positive | Positive |
| C. trachomatis 16s | Positive | Positive |
| E. coli LacZ 2 | Positive | Positive |
| Group 2: | | |
| E. coli SLT 1 | Negative | Positive |
| E. coli 16s | Positive | N/A |
| N. gonorrhea 16s | Positive | Positive |
| E. coli LacZ 1 | Positive | Negative |
| E. coli UIDA | Positive | Negative |
| 10 Primer Pair NASBA Boosted Simplex Reactions | | |
| E. coli SZ | Negative | Negative |
| E. coli SLT 2 | Negative | N/A |
| L. monocytogenes HlyA | Positive | Positive |
| C. trachomatis 16s | Positive | Positive |
| E. coli LacZ 2 | Positive | Positive |
| E. coli SLT 1 | Negative | Positive |
| E. coli 16s | Positive | N/A |
| N. gonorrhea 16s | Positive | Positive |
| E. coli LacZ 1 | Positive | Negative |
| E. coli UIDA | Positive | Negative |

Example 3

Detection of E. coli Using Sequences that Uniquely Identify E. coli

The E. coli gene lacZ coding for beta-galactosidase (EC 3.2.1.23) was for identifying sequences that uniquely identify E. coli. Various sequences of use in the detection of E. coli were located between base pairs 1700 to 1950 of the LacZ gene, identified as SEQ ID NO: 100 and shown below. Table 4 shows the lac Z gene sequences described by base pair number position relative to the E. coli genomic sequence in Genbank (accession VOO296, version VOO296.1 GI:41901).

SEQ ID NO: 100
TCTGGGACTGGGTGGATCAGTCGCTGATTAAATATGATGAAAACGGCAAC

CCGTGGTCGGCTTACGGCGGTGATTTTGGCGATACGCCGAACGATCGCCA

GTTCTGTATGAACGGTCTGGTCTTTGCCGACCGCACGCCGCATCCAGCGC

TGACGGAAGCAAAACACCAGCAGCAGTTTTTCCAGTTCCGTTTATCCGGG

CAAACCATCGAAGTGACCAGCGAATACCTGTTCCGTCATAGCGATAACGA

G

For specificity studies, nucleic acid was extracted onto Xtra Amp™ tubes (Xtrana, Inc, series III extraction kits) starting with high copy number (1,000,000 CFU) of various bacteria following a two hour induction with 1 mM isopropyl β-D-thiogalactopyranoside (IPTG) by the induction protocol described in detail below. The extracted nucleic acid was then NASBA amplified with various primer combinations. The specificity and specific bacterial strains are summarized in Table 5. The sequences confirmed to be specific only to E. coli is primer set 5085/5086, the sequences of which are shown in Table 4. In addition, sequence 5085 with T7 promoter sequences added for NASBA (SEQ ID NO. 97) was used, where SEQ ID NO: 97 is

5' AATTCTAATACGACTCACTATAGGGAGAGGACGGATAAACGGAACTGG
A.

Other primer pairs in this region were also specific to E. coli, with certain individual strain exceptions as detailed in Table 5.

TABLE 4

| Primer No | starting base pair | ending base pair | sense | SEQUENCE | SEQ ID NO: |
|---|---|---|---|---|---|
| 5085 | 1880 | 1897 | (−) | CGGATAAACGGAACTGGA | 85 |
| 5086 | 1733 | 1750 | (+) | ATGATGAAAACGGCAACC | 86 |
| 5100 | 1668 | 1687 | (+) | TCGTCAGTATCCCCGTTTAC | 87 |
| 5101 | 1909 | 1928 | (−) | AGGTATTCGCTGGTCACTTC | 88 |
| 5089 [a] | 1856 | 1872 | (−) | CTGCTGGTGTTTTGCTT | 89 |
| 5094 [a] | 1761 | 1782 | (+) | TTACGGCGGTGATTTTGGCGAT | 90 |
| 5064 [b] | 1866 | 1880 | (−) | GAAAACTGCTGCTGG | 91 |
| 5063 [b] | 1681 | 1702 | (+) | CGTTTACAGGGCGGCTTCGTCT | 92 |
| 5090 | 1866 | 1883 | (−) | GAAAAACTGCTGCTGGTGT | 93 |
| 5097 | 1880 | 1900 | (−) | GCCCGGATAAACGGAACTGGA | 94 |
| 5098 | 1721 | 1750 | (+) | CGCTGATTAAATATGATGAAAACGGCAACC | 95 |
| 5099 | 1733 | 1755 | (+) | ATGATGAAAACGGCAACCCGTGG | 96 |

[a] formerly LacZ 1 fp
[b] formerly LaeZ 2 fp

TABLE 5

| Primer Pair | Base Pairs | E. coli spp. | E. cloacae | E. aerogenes | C. fruendii | K. pneumoniae | S. austin | S. flexnerii |
|---|---|---|---|---|---|---|---|---|
| 5085 + 5086 | 1733-1897 | + | – | – | – | – | NT | – |
| 5101 + 5100 | 1668-1928 | + | + | – | – | – | NT | – |
| 5090 + 5063 | 1681-1866 | + | + | NT | – | – | NT | NT |
| 5085 + 5063 | 1681-1897 | + | + | NT | – | – | NT | NT |
| 5097 + 5098 | 1721-1900 | + | + | NT | – | + | NT | NT |
| 5063 + 5064 | 1681-1880 | + | + | NT | – | – | – | NT |
| 5097 + 5086 | 1733-1900 | + | + | NT | – | – | NT | NT |
| 5097 + 5099 | 1721-1900 | + | + | NT | – | – | NT | NT |

Induction and purification of lacZ mRNA from low copy cells diluted into water from cultures of E. coli bacteria was performed as follows. E. coli bacteria were routinely cultured on either LB (10 g/L tryptone, 5 g/L yeast extract, 10 g/L sodium chloride and 15 g/L agar) or TSA agar (15 g/L pancreatic digest of casein, 5 g/L enzymatic digest of soybean meal and 5 g/L sodium chloride, 15 g/L agar) medium at 37° C. Liquid cultures were routinely prepared in TSB (15 g/L pancreatic digest of casein and 5 g/L enzymatic digest of soybean meal, 5 g/L sodium chloride).

Small scale induction of lacZ mRNA was performed using 10% tryptone and 1 mM IPTG (isopropyl β-D-thio-galactopyranoside). A single colony of E. coli bacteria was inoculated into 3 mL of TSB culture medium in a 15 mL culture tube. The culture was grown overnight at 37° C. with shaking to approximately $1\times10^9$ colony forming units (cfu) per mL. The culture was diluted in 0.5×SSC buffer (7.5 mM sodium citrate (pH 7), 75 mM NaCl) and an aliquot containing one to approximately $10^6$ cfu was added to a 15 mL tube containing 500 µL 10% tryptone, 1 mM IPTG. The culture was incubated in a 37° C. water bath with shaking for about 2 to 6 hours to induce the lacZ mRNA target.

An aliquot of the induced culture (50 to 100 µL) was transferred to an XtraAmp® extraction tube. The culture was lysed with an equal volume of either XtraAmp® Series 2 lysis buffer (Xtrana, Inc.), or XtraAmp® Series 3 lysis buffer (Xtrana, Inc.). The lysis buffer was mixed briefly with the culture and incubated 10 minutes at room temperature. The liquid was removed from the tube, and the bound nucleic acid was washed twice with 100 µL volumes of either nuclease free water or XtraAmp Series 1 wash buffer.

NASBA amplification of a portion of the lacZ nucleic acid molecule using primers uniquely specific for the E. coli lacZ gene was performed as follows. For this specific example primers denoted herein as Primer No. 5085 (SEQ ID NO: 85) and Primer No. 5086 (SEQ ID NO: 86) were used. Primer No. 5085 contains 49 residues, the last 18 of which bind to a portion of the lacZ nucleic acid sequence in E. coli serovars (including enterotoxigenic strains, e.g. E. coli O157:H7). The first 31 residues of Primer No. 5085 contain nucleic acid information required for T7 RNA polymerase binding and transcription initiation. The nucleic acid sequence Primer No. 5086 contains 18 residues that specifically bind the E. coli lacZ nucleic acid sequence. Kit reagents provided in the Nuclisens Basic Kit (Biomerieux product No. 285053) were combined to produce two solutions: an enzyme solution, and a master mix solution containing 70 mM potassium chloride and 1.25 µM each of Primer No. 5085 and Primer No. 5086. Aliquots (15 µL) of the master mix were added to nucleic acid bound in XtraAmp tubes. The tubes were placed in a nucleic acid thermocycler or suitable heating instrument and incubated 2 minutes at 65° C. The tubes were cooled to 40° C. and 5 µL of enzyme solution was added to each tube. The tubes were heated for an additional 90 minutes at 40° C.

The aqueous solution following amplification was assayed by lateral flow as described below and as detailed in U.S. patent application Ser. No. 09/705,043, filed Nov. 2, 2000, which is specifically incorporated herein by reference. Lateral flow chromatographic detection results in a visible blue line on a nitrocellulose strip in the presence of the 230 base pair nucleic acid amplification product of E. coli lacZ mRNA using Primer Nos. 5085 and 5086. The detection primer set denoted herein as Detection Primer Mix No. 5097 contained Primer Nos. 5087 and 5088 at 1.25 µM each. The specific sequence of the detection probes were:

Primer No. 5087:
(SEQ ID NO: 98)
5'-FITC-GGTCGGCTTACGGCGGTG-phosphate

Primer No. 5088:
(SEQ ID NO: 99)
5'-CTGTATGAACGGTCTGGTCTTTG-Biotin.

Figure 4:
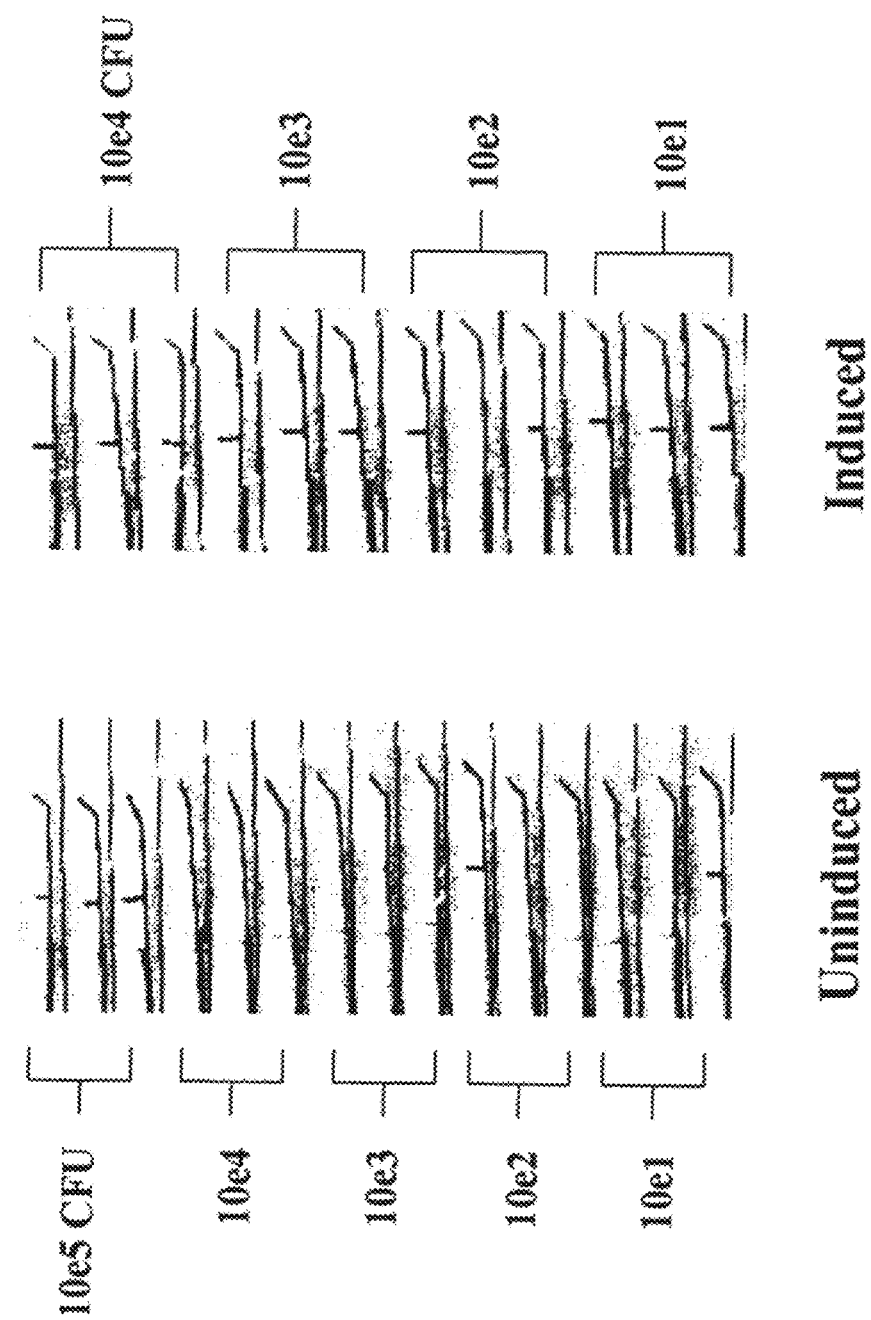
FIG. 4 shows the detection results of a lateral flow assay of uninduced and induced *E. coli* culture.

Primer No. 5087 includes 18 residues of the E. coli lacZ nucleic acid sequence. The 5' and 3' ends of Primer No. 5087 are modified with FITC (fluorescein isothiocyanate) and phosphate, respectively. Primer No. 5088 includes 23 residues of the E. coli lacZ nucleic acid sequence. The 3' portion of Primer No. 5088 was modified with a biotin molecule. A 10 µL portion of the NASBA reaction (described in Example 2) was transferred to a 0.5 mL tube. One uL of Detection Primer Mix No. 5088 and 40 µL of lateral flow buffer (50 mM TrisCl (pH 8), 8 mM $MgCl_2$, 0.25% Triton X-100, 0.8% PEG-8000) were added to 0.5 mL tube. The tube was mixed and incubated 1 minute at 95° C. The tube was cooled for 1 minute at room temperature, and the entire solution was applied to the sample pad of a lateral flow detection laminate containing embedded detection conjugates. The sample was allowed to wick through the lateral flow strip for approximately 5 minutes. Results were recorded visually. A blue-colored line indicated the presence of the lacZ nucleic acid sequence as illustrated in FIG. 4.

Using the above protocol following a two hours either with or without IPTG revealed a dramatic increase in detection sensitivity as a result of induction of lacZ mRNA transcription.

The foregoing description is considered as illustrative only of the principles of the invention. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily occur to those skilled in the art, it is not desired to limit the invention to the exact construction and process described above. Accordingly, all suitable modifications and equivalents may be resorted to falling within the scope of the invention as defined by the claims that follow.

The invention claimed is:

1. A method for simultaneously amplifying multiple nucleic acid targets, comprising:
   (a) contacting at least two primer pairs that target different nucleic acid sequences with multiple single stranded nucleic acid targets;
   (b) pre-amplifying said nucleic acid targets to about 100-1000 fold so that the reaction plateau is not reached;
   (c) dividing said pre-amplified targets into separate reaction chambers wherein the number of said chambers used is equal to the number of primer pairs; and
   (d) amplifying said pre-amplified targets;
   (e) detecting at least one target sequence in the divided pre-amplified sample.

2. The method of claim 1, wherein the single stranded nucleic acid targets are DNA polynucleotides and the polymerase is a DNA polymerase.

3. The method of claim 1, wherein said targets are in an aqueous solution.

4. The method of claim 1, wherein said targets are irreversibly bound to a solid phase matrix.

5. A two-step method for amplifying multiple nucleic acid sequence targets contained in a sample comprising:
   (a) performing a first round of amplification to form a plurality of first amplification products, comprising contacting the sample with a plurality of primer pairs specific to multiple nucleic acid sequence targets, wherein the first round of amplification is truncated prior to reaching a reaction plateau;

(b) dividing the plurality of first amplification products into at least two distinct aliquots; and, (c) performing a second round of amplification with each of the at least two distinct aliquots, comprising contacting the plurality of first amplification products with a primer pair specific to one of the multiple nucleic acid sequence targets amplified with the plurality of primer pairs in (a).

6. The method of claim 5, wherein the plurality of primer pairs include target specific primer pairs.

7. The method of claim 6, wherein at least one of the target specific primer pairs is complementary to human or bacterial gene targets.

8. The method of claim 5, wherein the plurality of first amplification products include nucleic acids from 100 base pairs to 1100 base pairs in length.

9. The method of claim 5, wherein the plurality of first amplification products contain nucleic acids having from 30% to 70% GC content.

10. The method of claim 5, wherein the first round of amplification includes performing a polymerase chain reaction.

11. The method of claim 5, wherein the first round of amplification includes performing an isothermal amplification reaction.

12. The method of claim 5, wherein the second round of amplification includes performing a polymerase chain reaction, strand displacement amplification or isothermal amplification.

13. The method of claim 5, further comprising (d) detecting at least one of the multiple nucleic acid sequence targets.

14. The method of claim 5, wherein at least one of the multiple nucleic acid sequence targets includes genomic DNA.

15. The method of claim 5, wherein at least one of the multiple nucleic acid sequence targets includes DNA or RNA extracted from tissue or culture samples.

16. The method of claim 5, wherein the first round of amplification is truncated by exhaustion of the plurality of primer pairs prior to reaching the amplification reaction plateau.

17. The method of claim 5, wherein the first round of amplification is truncated by limiting primer concentration of the plurality of primer pairs prior to reaching the amplification reaction plateau.

18. The method of claim 5, wherein the first round of amplification is truncated by limiting to only a few logs of amplification.

19. The method of claim 5, wherein the multiple nucleic acid sequence targets in (a) are amplified into early logarithmic phase.

20. The method of claim 5, wherein the second round of amplification comprises performing singleplex amplification reactions in each of the at least two distinct aliquots.

* * * * *

SEQUENCE LISTING

<160> NUMBER OF SEQ ID NOS: 100

<210> SEQ ID NO 1
<211> LENGTH: 15
<212> TYPE: DNA
<213> ORGANISM: Homo sapiens

<400> SEQUENCE: 1
cgaggcccag agcaa                                                     15

<210> SEQ ID NO 2
<211> LENGTH: 17
<212> TYPE: DNA
<213> ORGANISM: Homo sapiens

<400> SEQUENCE: 2
ggtgtggtgc cagattt                                                   17

<210> SEQ ID NO 3
<211> LENGTH: 17
<212> TYPE: DNA
<213> ORGANISM: Homo sapiens

<400> SEQUENCE: 3
gtttaatcag agccaca                                                   17

<210> SEQ ID NO 4
<211> LENGTH: 17
<212> TYPE: DNA
<213> ORGANISM: Homo sapiens

<400> SEQUENCE: 4
ggaaaggtag gtcaaga                                                   17

<210> SEQ ID NO 5
<211> LENGTH: 17
<212> TYPE: DNA
<213> ORGANISM: Homo sapiens

<400> SEQUENCE: 5
gtcttgcatt gcactaa                                                   17

<210> SEQ ID NO 6
<211> LENGTH: 17
<212> TYPE: DNA
<213> ORGANISM: Homo sapiens

<400> SEQUENCE: 6
taaatgtgag catcctg                                                   17

<210> SEQ ID NO 7
<211> LENGTH: 22
<212> TYPE: DNA
<213> ORGANISM: Homo sapiens

<400> SEQUENCE: 7
ctgtggaggg cagctgtggc tt                                             22

<210> SEQ ID NO 8
<211> LENGTH: 22
<212> TYPE: DNA
<213> ORGANISM: Homo sapiens

<400> SEQUENCE: 8

```
gcgggcggat tacctgaggt ca                                      22
```

<210> SEQ ID NO 9
<211> LENGTH: 17
<212> TYPE: DNA
<213> ORGANISM: Homo sapiens

<400> SEQUENCE: 9

```
tcagcagaga agcctaa                                            17
```

<210> SEQ ID NO 10
<211> LENGTH: 16
<212> TYPE: DNA
<213> ORGANISM: Homo sapiens

<400> SEQUENCE: 10

```
atccctaccc catcat                                             16
```

<210> SEQ ID NO 11
<211> LENGTH: 17
<212> TYPE: DNA
<213> ORGANISM: Homo sapiens

<400> SEQUENCE: 11

```
caaaagtcct cccaaag                                            17
```

<210> SEQ ID NO 12
<211> LENGTH: 18
<212> TYPE: DNA
<213> ORGANISM: Homo sapiens

<400> SEQUENCE: 12

```
tgccatctat cacaatcc                                           18
```

<210> SEQ ID NO 13
<211> LENGTH: 18
<212> TYPE: DNA
<213> ORGANISM: Homo sapiens

<400> SEQUENCE: 13

```
aagggtcatc atctctgc                                           18
```

<210> SEQ ID NO 14
<211> LENGTH: 19
<212> TYPE: DNA
<213> ORGANISM: Homo sapiens

<400> SEQUENCE: 14

```
cttccacgat accaaagtt                                          19
```

<210> SEQ ID NO 15
<211> LENGTH: 20
<212> TYPE: DNA
<213> ORGANISM: Homo sapiens

<400> SEQUENCE: 15

```
cgctttaagt tatttgtgtc                                         20
```

<210> SEQ ID NO 16
<211> LENGTH: 20
<212> TYPE: DNA
<213> ORGANISM: Homo sapiens

<400> SEQUENCE: 16
gtttcctttt aagggtattc                                              20

<210> SEQ ID NO 17
<211> LENGTH: 17
<212> TYPE: DNA
<213> ORGANISM: Homo sapiens

<400> SEQUENCE: 17
catctacgag gggtatg                                                 17

<210> SEQ ID NO 18
<211> LENGTH: 13
<212> TYPE: DNA
<213> ORGANISM: Homo sapiens

<400> SEQUENCE: 18
gccgtggtgg tga                                                     13

<210> SEQ ID NO 19
<211> LENGTH: 22
<212> TYPE: DNA
<213> ORGANISM: Homo sapiens

<400> SEQUENCE: 19
gtttgccttt tatggtaata ac                                           22

<210> SEQ ID NO 20
<211> LENGTH: 14
<212> TYPE: DNA
<213> ORGANISM: Homo sapiens

<400> SEQUENCE: 20
gtgagctgcg agaa                                                    14

<210> SEQ ID NO 21
<211> LENGTH: 20
<212> TYPE: DNA
<213> ORGANISM: Homo sapiens

<400> SEQUENCE: 21
gagtccactg gcgtcttcac                                              20

<210> SEQ ID NO 22
<211> LENGTH: 20
<212> TYPE: DNA
<213> ORGANISM: Homo sapiens

<400> SEQUENCE: 22
aggctgttgt catacttctc                                              20

<210> SEQ ID NO 23
<211> LENGTH: 17
<212> TYPE: DNA
<213> ORGANISM: Homo sapiens

<400> SEQUENCE: 23 ccacccccctt aaagaaa                                                17

<210> SEQ ID NO 24
<211> LENGTH: 17
<212> TYPE: DNA
<213> ORGANISM: Homo sapiens

```
<400> SEQUENCE: 24
ggcaggagtt gaggtta                                                    17

<210> SEQ ID NO 25
<211> LENGTH: 22
<212> TYPE: DNA
<213> ORGANISM: Homo sapiens

<400> SEQUENCE: 25
gcggggagga ggaaaggaat ag                                              22

<210> SEQ ID NO 26
<211> LENGTH: 22
<212> TYPE: DNA
<213> ORGANISM: Homo sapiens

<400> SEQUENCE: 26
caggacacat tgtgccaaag gg                                              22

<210> SEQ ID NO 27
<211> LENGTH: 17
<212> TYPE: DNA
<213> ORGANISM: Homo sapiens

<400> SEQUENCE: 27
ccactattcg gaaactt                                                    17

<210> SEQ ID NO 28
<211> LENGTH: 17
<212> TYPE: DNA
<213> ORGANISM: Homo sapiens

<400> SEQUENCE: 28
tgtatggcat aatgaca                                                    17

<210> SEQ ID NO 29
<211> LENGTH: 20
<212> TYPE: DNA
<213> ORGANISM: Homo sapiens

<400> SEQUENCE: 29
gagtcgaggg atggctaggt                                                 20

<210> SEQ ID NO 30
<211> LENGTH: 20
<212> TYPE: DNA
<213> ORGANISM: Homo sapiens

<400> SEQUENCE: 30
ttcaaagtgg gatgaggagg                                                 20

<210> SEQ ID NO 31
<211> LENGTH: 18
<212> TYPE: DNA
<213> ORGANISM: Homo sapiens

<400> SEQUENCE: 31
ggactgccac cttctacc                                                   18

<210> SEQ ID NO 32
<211> LENGTH: 18
<212> TYPE: DNA
```

<213> ORGANISM: Homo sapiens

<400> SEQUENCE: 32
gacacccaag catacacc                                                    18

<210> SEQ ID NO 33
<211> LENGTH: 22
<212> TYPE: DNA
<213> ORGANISM: Homo sapiens

<400> SEQUENCE: 33
gcagatgagc atacgctgag tg                                               22

<210> SEQ ID NO 34
<211> LENGTH: 22
<212> TYPE: DNA
<213> ORGANISM: Homo sapiens

<400> SEQUENCE: 34 cgagggggaaa tgaagaatac gg                                              22

<210> SEQ ID NO 35
<211> LENGTH: 17
<212> TYPE: DNA
<213> ORGANISM: Homo sapiens

<400> SEQUENCE: 35
aggggaggtg atagcat                                                     17

<210> SEQ ID NO 36
<211> LENGTH: 16
<212> TYPE: DNA
<213> ORGANISM: Homo sapiens

<400> SEQUENCE: 36
aagttggggg acaaaa                                                      16

<210> SEQ ID NO 37
<211> LENGTH: 18
<212> TYPE: DNA
<213> ORGANISM: Homo sapiens

<400> SEQUENCE: 37
ccggtgccat cttccata                                                    18

<210> SEQ ID NO 38
<211> LENGTH: 18
<212> TYPE: DNA
<213> ORGANISM: Homo sapiens

<400> SEQUENCE: 38
cctgccttgc ccattctt                                                    18

<210> SEQ ID NO 39
<211> LENGTH: 17
<212> TYPE: DNA
<213> ORGANISM: Homo sapiens

<400> SEQUENCE: 39
gaggggagag ggggtaa                                                     17

<210> SEQ ID NO 40
<211> LENGTH: 13

<212> TYPE: DNA
<213> ORGANISM: Homo sapiens

<400> SEQUENCE: 40
cggcgggtgt gga                                                          13

<210> SEQ ID NO 41
<211> LENGTH: 18
<212> TYPE: DNA
<213> ORGANISM: Homo sapiens

<400> SEQUENCE: 41
ggctgctttt aactctgg                                                     18

<210> SEQ ID NO 42
<211> LENGTH: 22
<212> TYPE: DNA
<213> ORGANISM: Homo sapiens

<400> SEQUENCE: 42
cactcctgga agatggtgat gg                                                22

<210> SEQ ID NO 43
<211> LENGTH: 20
<212> TYPE: DNA
<213> ORGANISM: Homo sapiens

<400> SEQUENCE: 43
ctcattctct agccaaatct                                                   20

<210> SEQ ID NO 44
<211> LENGTH: 18
<212> TYPE: DNA
<213> ORGANISM: Homo sapiens

<400> SEQUENCE: 44
cctcgactca ctctcctc                                                     18

<210> SEQ ID NO 45
<211> LENGTH: 22
<212> TYPE: DNA
<213> ORGANISM: Homo sapiens

<400> SEQUENCE: 45
ctatcgccat ctaagcccag ta                                                22

<210> SEQ ID NO 46
<211> LENGTH: 20
<212> TYPE: DNA
<213> ORGANISM: Homo sapiens

<400> SEQUENCE: 46
ctgcctgcat tttcacttca                                                   20

<210> SEQ ID NO 47
<211> LENGTH: 50
<212> TYPE: DNA
<213> ORGANISM: Chlamydia trachomatis

<400> SEQUENCE: 47
aattctaata cgactcacta tagggagagg taaccgaaag gtcctaagat                  50

<210> SEQ ID NO 48

```
<211> LENGTH: 20
<212> TYPE: DNA
<213> ORGANISM: Chlamydia trachomatis

<400> SEQUENCE: 48
attgtttagt ggcggaaggg                                              20

<210> SEQ ID NO 49
<211> LENGTH: 22
<212> TYPE: DNA
<213> ORGANISM: Chlamydia trachomatis

<400> SEQUENCE: 49
acttgggaat aacggttgga aa                                           22

<210> SEQ ID NO 50
<211> LENGTH: 22
<212> TYPE: DNA
<213> ORGANISM: Chlamydia trachomatis

<400> SEQUENCE: 50
gctaataccg aatgtggcga ta                                           22

<210> SEQ ID NO 51
<211> LENGTH: 50
<212> TYPE: DNA
<213> ORGANISM: Neisseria gonorrhoeae

<400> SEQUENCE: 51
aattctaata cgactcacta tagggagaac tgacatcgtt tagggcgtgg             50

<210> SEQ ID NO 52
<211> LENGTH: 20
<212> TYPE: DNA
<213> ORGANISM: Neisseria gonorrhoeae

<400> SEQUENCE: 52
aatgcgtaga gatgtggagg                                              20

<210> SEQ ID NO 53
<211> LENGTH: 23
<212> TYPE: DNA
<213> ORGANISM: Neisseria gonorrhoeae

<400> SEQUENCE: 53
agcctcctgg gataacactg acg                                          23

<210> SEQ ID NO 54
<211> LENGTH: 25
<212> TYPE: DNA
<213> ORGANISM: Neisseria gonorrhoeae

<400> SEQUENCE: 54
agcgtgggta gcaaacagga ttaga                                        25

<210> SEQ ID NO 55
<211> LENGTH: 53
<212> TYPE: DNA
<213> ORGANISM: Escherichia coli

<400> SEQUENCE: 55
aattctaata cgactcacta tagggagagg aaactgctgc tggtgttttg ctt         53
```

```
<210> SEQ ID NO 56
<211> LENGTH: 22
<212> TYPE: DNA
<213> ORGANISM: Escherichia coli

<400> SEQUENCE: 56
ttacggcggt gattttggcg at                                              22

<210> SEQ ID NO 57
<211> LENGTH: 18
<212> TYPE: DNA
<213> ORGANISM: Escherichia coli

<400> SEQUENCE: 57
atcgccagtt ctgtatga                                                   18

<210> SEQ ID NO 58
<211> LENGTH: 22
<212> TYPE: DNA
<213> ORGANISM: Escherichia coli

<400> SEQUENCE: 58
ccgaccgcac gccgcatcca gc                                              22

<210> SEQ ID NO 59
<211> LENGTH: 52
<212> TYPE: DNA
<213> ORGANISM: Escherichia coli

<400> SEQUENCE: 59
attctaatac gactcactat agggagagga gaactggaaa aactgctgct gg             52

<210> SEQ ID NO 60
<211> LENGTH: 22
<212> TYPE: DNA
<213> ORGANISM: Escherichia coli

<400> SEQUENCE: 60
cgtttacagg gcggcttcgt ct                                              22

<210> SEQ ID NO 61
<211> LENGTH: 18
<212> TYPE: DNA
<213> ORGANISM: Escherichia coli

<400> SEQUENCE: 61
atcgccagtt ctgtatga                                                   18

<210> SEQ ID NO 62
<211> LENGTH: 22
<212> TYPE: DNA
<213> ORGANISM: Escherichia coli

<400> SEQUENCE: 62
ccgaccgcac gccgcatcca gc                                              22

<210> SEQ ID NO 63
<211> LENGTH: 56
<212> TYPE: DNA
<213> ORGANISM: Coliform Bacteria

<400> SEQUENCE: 63
aattctaata cgactcacta tagggagagg aatagtctgc cagttcagtt cgttgt         56
```

```
<210> SEQ ID NO 64
<211> LENGTH: 25
<212> TYPE: DNA
<213> ORGANISM: Coliform Bacteria

<400> SEQUENCE: 64
caaagtgtgg gtcaataatc aggaa                                   25

<210> SEQ ID NO 65
<211> LENGTH: 22
<212> TYPE: DNA
<213> ORGANISM: Coliform Bacteria

<400> SEQUENCE: 65
ctatacgcca tttgaagccg at                                      22

<210> SEQ ID NO 66
<211> LENGTH: 22
<212> TYPE: DNA
<213> ORGANISM: Coliform Bacteria

<400> SEQUENCE: 66
gtcacgccgt atgttattgc cg                                      22

<210> SEQ ID NO 67
<211> LENGTH: 23
<212> TYPE: DNA
<213> ORGANISM: Escherichia coli

<400> SEQUENCE: 67
ttgttagcgt tacgtttccc tct                                     23

<210> SEQ ID NO 68
<211> LENGTH: 58
<212> TYPE: DNA
<213> ORGANISM: Escherichia coli

<400> SEQUENCE: 68
aattctaata cgactcacta tagggagag gataatacca aatcaggttt tccattga    58

<210> SEQ ID NO 69
<211> LENGTH: 24
<212> TYPE: DNA
<213> ORGANISM: Escherichia coli

<400> SEQUENCE: 69
cgatgatgct acccctgaaa aact                                    24

<210> SEQ ID NO 70
<211> LENGTH: 24
<212> TYPE: DNA
<213> ORGANISM: Escherichia coli

<400> SEQUENCE: 70
gagaatgaaa tagaagtcgt tgtt                                    24

<210> SEQ ID NO 71
<211> LENGTH: 21
<212> TYPE: DNA
<213> ORGANISM: Escherichia coli O157:H7

<400> SEQUENCE: 71
gtttgcagtt gatgtcagag g                                       21
```

```
<210> SEQ ID NO 72
<211> LENGTH: 49
<212> TYPE: DNA
<213> ORGANISM: Escherichia coli O157:H7

<400> SEQUENCE: 72
attctaatac gactcactat agggagagga acgtggtata gctactgtc            49

<210> SEQ ID NO 73
<211> LENGTH: 25
<212> TYPE: DNA
<213> ORGANISM: Escherichia coli O157:H7

<400> SEQUENCE: 73
atctacggct tattgttgaa cgaaa                                      25

<210> SEQ ID NO 74
<211> LENGTH: 25
<212> TYPE: DNA
<213> ORGANISM: Escherichia coli O157:H7

<400> SEQUENCE: 74
ttttatcgct ttgctgattt ttcac                                      25

<210> SEQ ID NO 75
<211> LENGTH: 20
<212> TYPE: DNA
<213> ORGANISM: Escherichia coli

<400> SEQUENCE: 75
ttgctgtgga tatacgaggg                                            20

<210> SEQ ID NO 76
<211> LENGTH: 49
<212> TYPE: DNA
<213> ORGANISM: Escherichia coli

<400> SEQUENCE: 76
attctaatac gactcactat agggagagga gagtggtata actgctgtc            49

<210> SEQ ID NO 77
<211> LENGTH: 25
<212> TYPE: DNA
<213> ORGANISM: Escherichia coli

<400> SEQUENCE: 77
ttttgaccat cttcgtctga ttatt                                      25

<210> SEQ ID NO 78
<211> LENGTH: 25
<212> TYPE: DNA
<213> ORGANISM: Escherichia coli

<400> SEQUENCE: 78
gttaatacgg caacaaatac tttct                                      25

<210> SEQ ID NO 79
<211> LENGTH: 53
<212> TYPE: DNA
<213> ORGANISM: Universal

<400> SEQUENCE: 79
```

```
aattctaata cgactcacta tagggagagg accttgttac gacttcaccc cag        53
```

<210> SEQ ID NO 80
<211> LENGTH: 22
<212> TYPE: DNA
<213> ORGANISM: Universal

<400> SEQUENCE: 80

```
tacacaccgc ccgtcacacc at                                          22
```

<210> SEQ ID NO 81
<211> LENGTH: 47
<212> TYPE: DNA
<213> ORGANISM: Listeria monocytogenes

<400> SEQUENCE: 81

```
aattctaata cgactcacta tagggagaac cttttcttgg cggcaca               47
```

<210> SEQ ID NO 82
<211> LENGTH: 20
<212> TYPE: DNA
<213> ORGANISM: Listeria monocytogenes

<400> SEQUENCE: 82

```
gtcctaagac gccaatcgaa                                             20
```

<210> SEQ ID NO 83
<211> LENGTH: 27
<212> TYPE: DNA
<213> ORGANISM: Listeria monocytogenes

<400> SEQUENCE: 83

```
aacacgctga tgaaatctat aagtata                                     27
```

<210> SEQ ID NO 84
<211> LENGTH: 27
<212> TYPE: DNA
<213> ORGANISM: Listeria monocytogenes

<400> SEQUENCE: 84

```
gtattagtat accacggaga tgcagtg                                     27
```

<210> SEQ ID NO 85
<211> LENGTH: 18
<212> TYPE: DNA
<213> ORGANISM: Escherichia coli

<400> SEQUENCE: 85

```
cggataaacg gaactgga                                               18
```

<210> SEQ ID NO 86
<211> LENGTH: 18
<212> TYPE: DNA
<213> ORGANISM: Escherichia coli

<400> SEQUENCE: 86

```
atgatgaaaa cggcaacc                                               18
```

<210> SEQ ID NO 87
<211> LENGTH: 20
<212> TYPE: DNA
<213> ORGANISM: Escherichia coli

<400> SEQUENCE: 87

-continued

```
tcgtcagtat ccccgtttac                                              20

<210> SEQ ID NO 88
<211> LENGTH: 20
<212> TYPE: DNA
<213> ORGANISM: Escherichia coli

<400> SEQUENCE: 88
aggtattcgc tggtcacttc                                              20

<210> SEQ ID NO 89
<211> LENGTH: 17
<212> TYPE: DNA
<213> ORGANISM: Escherichia coli

<400> SEQUENCE: 89
ctgctggtgt tttgctt                                                 17

<210> SEQ ID NO 90
<211> LENGTH: 22
<212> TYPE: DNA
<213> ORGANISM: Escherichia coli

<400> SEQUENCE: 90
ttacggcggt gattttggcg at                                           22

<210> SEQ ID NO 91
<211> LENGTH: 15
<212> TYPE: DNA
<213> ORGANISM: Escherichia coli

<400> SEQUENCE: 91
gaaaactgct gctgg                                                   15

<210> SEQ ID NO 92
<211> LENGTH: 22
<212> TYPE: DNA
<213> ORGANISM: Escherichia coli

<400> SEQUENCE: 92
cgtttacagg gcggcttcgt ct                                           22

<210> SEQ ID NO 93
<211> LENGTH: 19
<212> TYPE: DNA
<213> ORGANISM: Escherichia coli

<400> SEQUENCE: 93
gaaaaactgc tgctggtgt                                               19

<210> SEQ ID NO 94
<211> LENGTH: 21
<212> TYPE: DNA
<213> ORGANISM: Escherichia coli

<400> SEQUENCE: 94
gcccggataa acggaactgg a                                            21

<210> SEQ ID NO 95
<211> LENGTH: 30
<212> TYPE: DNA
<213> ORGANISM: Escherichia coli
```

```
<400> SEQUENCE: 95
cgctgattaa atatgatgaa aacggcaacc                                            30

<210> SEQ ID NO 96
<211> LENGTH: 23
<212> TYPE: DNA
<213> ORGANISM: Escherichia coli

<400> SEQUENCE: 96
atgatgaaaa cggcaacccg tgg                                                   23

<210> SEQ ID NO 97
<211> LENGTH: 49
<212> TYPE: DNA
<213> ORGANISM: Escherichia coli

<400> SEQUENCE: 97
aattctaata cgactcacta tagggagagg acggataaac ggaactgga                       49

<210> SEQ ID NO 98
<211> LENGTH: 18
<212> TYPE: DNA
<213> ORGANISM: Escherichia coli

<400> SEQUENCE: 98
ggtcggctta cggcggtg                                                         18

<210> SEQ ID NO 99
<211> LENGTH: 23
<212> TYPE: DNA
<213> ORGANISM: Escherichia coli

<400> SEQUENCE: 99
ctgtatgaac ggtctggtct ttg                                                   23

<210> SEQ ID NO 100
<211> LENGTH: 251
<212> TYPE: DNA
<213> ORGANISM: Escherichia coli

<400> SEQUENCE: 100
tctgggactg ggtggatcag tcgctgatta aatatgatga aaacggcaac ccgtggtcgg           60
cttacggcgg tgattttggc gatacgccga acgatcgcca gttctgtatg aacggtctgg          120
tctttgccga ccgcacgccg catccagcgc tgacggaagc aaaacaccag cagcagtttt          180
tccagttccg tttatccggg caaaccatcg aagtgaccag cgaatacctg ttccgtcata          240
gcgataacga g                                                              251
```